(12) United States Patent
Martin et al.

(10) Patent No.: US 11,754,521 B2
(45) Date of Patent: Sep. 12, 2023

(54) SYSTEMS AND METHODS FOR LOW-POWER GAS MONITORING

(71) Applicant: Rutgers, The State University of New Jersey, New Brunswick, NJ (US)

(72) Inventors: Richard Martin, Metuchen, NJ (US); Richard Howard, Highland Park, NJ (US); Yanyong Zhang, Metuchen, NJ (US); Zhenhua Jia, Hoboken, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 346 days.

(21) Appl. No.: 17/190,119

(22) Filed: Mar. 2, 2021

(65) Prior Publication Data

US 2021/0181134 A1 Jun. 17, 2021

Related U.S. Application Data

(63) Continuation of application No. PCT/US2019/051837, filed on Sep. 19, 2019.
(Continued)

(51) Int. Cl.
G01N 27/12 (2006.01)
G01N 33/00 (2006.01)
G06N 3/044 (2023.01)

(52) U.S. Cl.
CPC ....... G01N 27/125 (2013.01); G01N 33/0006 (2013.01); G06N 3/044 (2023.01)

(58) Field of Classification Search
CPC ............. G01N 27/125; G01N 33/0006; G01N 2033/0068; G01N 27/12; G06N 3/044
See application file for complete search history.

(56) References Cited

U.S. PATENT DOCUMENTS 4,916,935 A * 4/1990 Novack ................... G01N 27/12
73/31.06
2007/0261959 A1* 11/2007 Kim ...................... G01N 27/127
427/190
(Continued)

OTHER PUBLICATIONS

International Search Report and Written Opinion in corresponding International PCT Application No. PCT/US2019/051837, dated Dec. 3, 2019, 9 pages.
(Continued)

*Primary Examiner* — Manuel A Rivera Vargas
(74) *Attorney, Agent, or Firm* — Greenberg Traurig, LLP

(57) ABSTRACT

Systems and methods of applying a prediction model to metal oxide sensors that change their electric resistances in response to surrounding gas concentrations for predicting equilibrium state resistance values of the sensors. The method includes heating a metal oxide sensor to for a predetermined period of time for the metal oxide sensor to interact with a surrounding gas; sampling transient resistance values of the metal oxide sensor to obtain sampled transient resistance values; determining an electrical resistance of the metal oxide sensor in a chemical equilibrium state of the interaction of the metal oxide sensor and the surrounding gas via applying a neural network; and determining a concentration level of the surrounding gas at the chemical equilibrium state by mapping the determined electrical resistance to a corresponding concentration level of the surrounding gas.

23 Claims, 14 Drawing Sheets

Related U.S. Application Data

(60) Provisional application No. 62/733,613, filed on Sep. 19, 2018.

(56) References Cited

U.S. PATENT DOCUMENTS

| | | |
|---|---|---|
| 2017/0031578 A1 | 2/2017 | Shakespeare et al. |
| 2017/0276627 A1* | 9/2017 | Dobrokhotov ....... G01N 27/125 |
| 2018/0365559 A1* | 12/2018 | Tayebi ............... G01N 33/0047 |

OTHER PUBLICATIONS

Baskar et al., "A Low Power Ammonia Sensor Node Embedded with a Light Weight Non-Linear Analytics", Sensors and Actuators A, Physical 263, Aug. 15, 2017, pp. 357-362.

Galdikas et al., "Response Time Based Output of Metal Oxide Gas Sensors Applied to Evaluation of Meat Freshness with Neural Signal Analysis", Sensors and Actuators B, Chemical 69.3, Oct. 25, 2000, pp. 258-265.

Jha et al., "Odor Filtering and Sensing System Based Artificial Nose for Chemical Vapor Class Recognition", Sensor letters 12.1, Jan. 1, 2014, pp. 1-16.

Jia et al., "Continuous Low-Power Ammonia Monitoring Using Long Short-Term Memory Neural Networks", Proceedings of the 16th ACM Conference on Embedded Networked Sensor Systems, ACM, Nov. 4, 2018.

* cited by examiner

SYSTEMS AND METHODS FOR LOW-POWER GAS MONITORING

CROSS-REFERENCE TO RELATED APPLICATION

This application is a continuation application relating to and claiming the benefit of commonly-owned, co-pending PCT International Application No. PCT/US2019/051837, filed Sep. 19, 2019, entitled "SYSTEMS AND METHODS FOR LOW-POWER GAS MONITORING," which claims priority to and the benefit of U.S. Provisional Patent Application Ser. No. 62/733,613 filed Sep. 19, 2018, entitled "SYSTEMS AND METHODS FOR LOW-POWER GAS MONITORING," the contents of each of the foregoing are herein incorporated by reference in its entirety.

FIELD OF INVENTION

The present disclosure generally relates to systems and methods of gas monitoring, and specifically relates to systems and methods of applying a prediction model to metal oxide sensors that change their electric resistances in response to surrounding gas concentrations for predicting equilibrium state resistance values of the sensors.

BACKGROUND

Accurate and continuous gas monitoring is important for laboratory animal studies and many other applications. Existing solutions are often expensive, inaccurate, or unsuitable for long-term monitoring. Traditional methods infer a level of concentration of ammonia by measuring a sensor's electrical resistance after it reaches equilibrium. Such a system consumes a significant amount of energy because reaching equilibrium requires heating the sensor for minutes.

SUMMARY OF THE INVENTION

In an embodiment, a system and approach for gas monitoring that is low-power, automatic, accurate, and wireless. In some embodiments, an exemplary application is for a metal oxide sensor paired with an algorithm model which utilizes a neural network. In an embodiment, the neural network is suitable for time-dependent data, including, but not limited to, Recurrent Neural Networks (RNNs). In an embodiment, the RNN includes a Long Short-Term Memory (LSTM) network. In an embodiment, the neural network accurately predicts environmental gas concentration.

Current methods of gas detection involve heating a metal oxide sensor for 5-10 minutes (420 seconds on average) at 300° C. and measuring the sensor's electrical resistance once it reaches equilibrium.

In an embodiment, the system uses metal oxide sensors which change their electrical resistance as a function of the gas concentration when heated. Instead of waiting for an equilibrium state, the developed technology as described in the present invention enables accurate prediction of gas concentrations at equilibrium based on the sensor's initial resistance response curve, which is generated after transiently heating the sensor for only a brief period (~200 milliseconds). In an embodiment, the system feeds the response curve into a prediction model built using the LSTM neural network.

In an embodiment, reducing the heating time to a fraction of what is needed for conventional ammonia sensors produces a substantial reduction in the sensor's energy requirements and an increase of the sensor life, making it possible to produce a wireless ammonia sensor utilizing only conventional batteries.

In an embodiment, the prediction model based on the LSTM neural networks focuses on the sensor's transient resistance measurements in a short time window and can accurately predict the final resistance value at the chemical equilibrium state which takes minutes to achieve. In an embodiment, the system precisely controls the heating power and duration, and accurately measures the sensor's transient resistance values in analog-to-digital converter (ADC) samples.

In an embodiment, the system accurately predicts the equilibrium state resistance value with an average error rate of 0.12% of the actual oxide resistance at equilibrium, using a factor of 99% less energy than the traditional method, which is two orders of magnitude reduction in energy consumption of metal oxide sensor-based gas measurement.

In an embodiment, the system is commercially relevant in facilities which conduct ongoing monitoring of gas concentration levels, such as animal research facilities and in industrial and manufacturing settings.

In an embodiment, a method includes the steps of heating a metal oxide sensor for a predetermined period of time for the metal oxide sensor to interact with a surrounding gas, wherein the metal oxide sensor includes a heater; sampling, during the heating, transient resistance values of the metal oxide sensor to obtain sampled transient resistance values; determining an electrical resistance of the metal oxide sensor in a chemical equilibrium state of the interaction of the metal oxide sensor and the surrounding gas, wherein determining the equilibrium electrical resistance is based at least upon the sampled transient resistance values and via applying a neural network; and determining a concentration level of the surrounding gas at the chemical equilibrium state by mapping the determined electrical resistance to a corresponding concentration level of the surrounding gas.

In an embodiment, the metal oxide sensor is heated to a temperature between 100 to 400° C. In an embodiment, the predetermined period of time is between 1-200 milliseconds. In an embodiment, the chemical equilibrium is when a metal oxide on a sensing layer of the metal oxide sensor reduction-oxidation ("redox") reacts with the surrounding gas and oxygen simultaneously and the redox process reaches its chemical equilibrium. In an embodiment, the transient resistance values of the metal oxide sensor are analog-to-digital converter (ADC) values and the predicted electrical resistance is a final ADC value of the metal oxide sensor.

In an embodiment, the step of sampling the transient resistance values includes: activating the metal oxide sensor; activating, by the metal oxide sensor, the heater inside of the metal oxide sensor; measuring the transient resistance values at a predetermined power during a first period of time; collecting the transient resistance values that are transient responses; deactivating, by the metal oxide sensor, the heater; and deactivating the metal oxide sensor for a second period of time till a next duty cycle. In an embodiment, wherein the first period of time is a first second of heating the metal oxide sensor. In an embodiment, wherein the second period of time is with a range from 10 minutes to 1 day. In an embodiment, wherein the sampled transient values are transmitted wirelessly before being preprocessed.

In an embodiment, the method further includes the steps of preprocessing the sampled transient resistance values, wherein the preprocessing comprises eliminating the sampled transient values from measurements that do not have a first 5 transient resistance samples or the final sample; and recovering missing data from transmission of the sampled transient resistance values by applying a spline interpolation technique. In an embodiment, the neural network is a long short term memory (LSTM) neural network. In an embodiment, the LSTM neural network includes an LSTM layer and a fully connected layer. In an embodiment, the LSTM layer at time n processes an input data $x_n$ together with cell state $c_{n-1}$ and previous output $h_{n-1}$, and sends output $h_n$ to the fully connected layer, and the fully connected layer generates a final output for the LSTM neural network. In an embodiment, the step of determining the electrical resistance of the metal oxide sensor in the chemical equilibrium state via applying the LSTM neural network comprises preparing the sampled transient resistance values to make them suitable for the LSTM neural network.

In an embodiment, the step of preparing the sampled transient resistance values comprises: computing first derivatives of the sampled transient resistance values configured to cause the LSTM neural network to learn desired patterns from the sampled transient resistance values; and scaling the computed derivative to a numerical range. In an embodiment, the surrounding gas is selected from a group of gases consisting of: ammonia, ethanol, hydrogen sulphide, methane, propane, iso-butane, nitrogen dioxide, and carbon monoxide.

In an embodiment, the step of mapping the determined electrical resistance at the chemical equilibrium to the corresponding gas concentration level comprises: placing multiple sensors into a container with fresh air, wherein the container has one gas connector on each side and has high corrosive resistance to the surrounding gas; connecting one of the gas connectors to a valve controlled cylinder that contains calibrated gas while leaving the other one of the gas connectors to the open air; continuously releasing the calibrated gas until the calibrated gas in the container reaches a same gas concentration as that inside of the valve controlled cylinder; repeating the placing, connecting, continuously releasing steps with different gas concentration levels; and fitting the different gas concentration levels into a curve-fitting model.

In an embodiment, a system includes a metal oxide sensor comprising a heater, an embedded heating layer, and a sensing layer, wherein the sensing layer is configured to interact with a surrounding gas and the heater is configured to heat the embedded heating layer for a predetermined period of time for the metal oxide sensor to interact with the surrounding gas; a processor; a non-transitory computer readable storage medium storing thereon program logic for execution by the processor, wherein, when executing the program logic, the processor is configured to: heat a metal oxide sensor to for a predetermined period of time for the metal oxide sensor to interact with a surrounding gas, wherein the metal oxide sensor comprising a heater; sample, during the heating, transient resistance values of the metal oxide sensor to obtain sampled transient resistance values; determine an electrical resistance of the metal oxide sensor in a chemical equilibrium state of the interaction of the metal oxide sensor and the surrounding gas to calculate a determined electrical resistance, wherein determining is based at least upon the sampled transient resistance values and via applying a neural network; and determine a concentration level of the surrounding gas at the chemical equilibrium state by mapping the determined electrical resistance to a corresponding concentration level of the surrounding gas.

In an embodiment, the metal oxide sensor further comprises a machined diaphragm base layer. In an embodiment, the processor is configured to sample the transient resistance values comprises: activate the metal oxide sensor; activate, by the metal oxide sensor, the heater inside of the metal oxide sensor; measure the transient resistance values at a predetermined power during a first period of time; collect the transient resistance values that are transient responses; deactivate, by the metal oxide sensor, the heater; and deactivate the metal oxide sensor for a second period of time till a next duty cycle.

In an embodiment, the processor is configured to determine the concentration level of the surrounding gas at the chemical equilibrium state by mapping the determined electrical resistance to a corresponding concentration level of the surrounding gas comprises: place multiple sensors into a container with fresh air, wherein the container has one gas connector on each side and has high corrosive resistance to the surrounding gas; connect one of the gas connectors to a valve controlled cylinder that contains calibrated gas while leaving the other one of the gas connectors to the open air; continuously release the calibrated gas until the calibrated gas in the container reaches a same gas concentration as that inside of the valve controlled cylinder; repeating the place, connect, continuously release steps with different gas concentration levels; and fit the different gas concentration levels into a curve-fitting model.

In an embodiment, the neural network is a long short term memory (LSTM) neural network. In an embodiment, the LSTM neural network includes an LSTM layer and a fully connected layer.

BRIEF DESCRIPTION OF THE DRAWINGS

FIG. 15(a) shows the transient response of a frequently used sensor having an obvious peak at around 0.2 s; FIG. 15(b) shows the transient response of a sensor that has not been used for a long time that may only have an increasing trend; and FIG. 15(c) shows multiple transient responses for the same ammonia concentration, when in all 3 plots, circles mark the equilibrium ADC sample at 100 s;

DETAILED DESCRIPTION

Figure 1A:
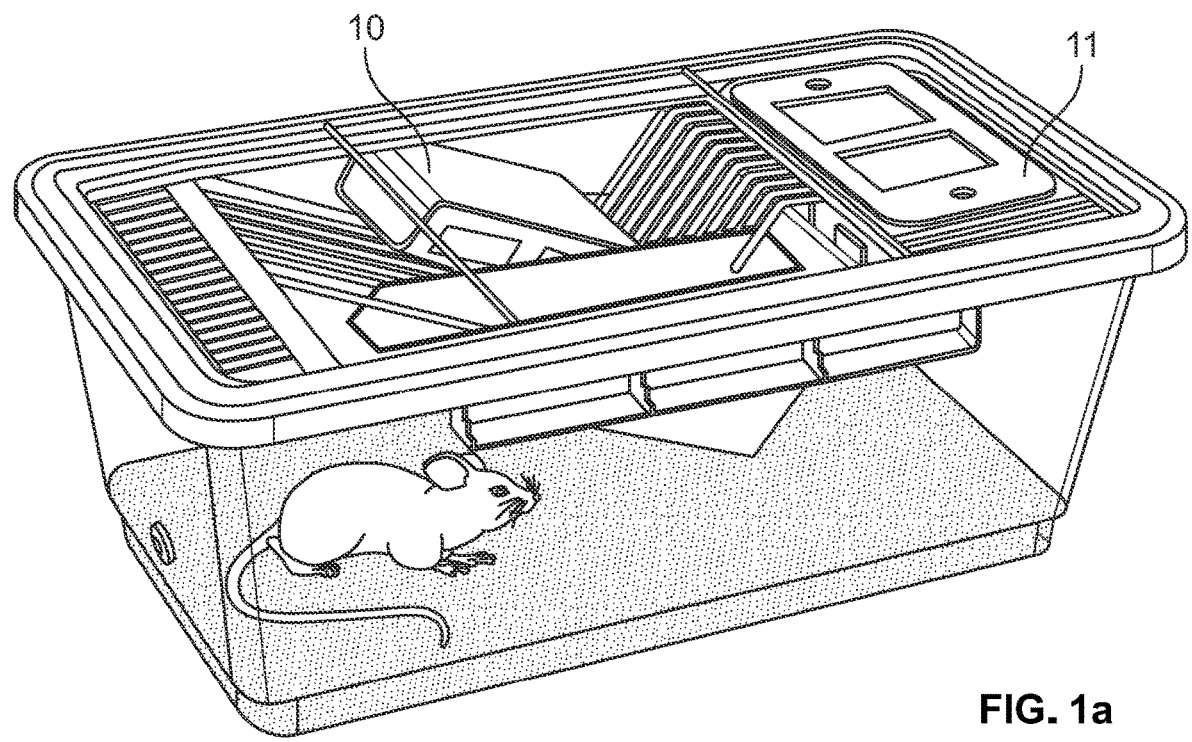
FIG. 1(a) is a cage with an embodiment of a gas monitoring system and FIG. 1(b) is a rack holding a plurality of cages.

The present invention can be further explained with reference to the included drawings, wherein like structures are referred to by like numerals throughout the several views. The drawings shown are not necessarily to scale, with emphasis instead generally being placed upon illustrating the principles of the present invention. Therefore, specific structural and functional details disclosed herein are not to be interpreted as limiting, but merely as a representative basis for teaching one skilled in the art to variously employ the present invention.

Among those benefits and improvements that have been disclosed, other objects and advantages of this invention can become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the present invention is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though they may. Furthermore, the phrases "in another embodiment" and "in some other embodiments" as used herein do not necessarily refer to a different embodiment, although they may. Thus, as described below, various embodiments of the invention may be readily combined, without departing from the scope or spirit of the invention. Further, when a particular feature, structure, or characteristic is described in connection with an implementation, it is submitted that it is within the knowledge of one skilled in the art to effect such feature, structure, or characteristic in connection with other implementations whether or not explicitly described herein.

The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

In some embodiments, the inventive specially programmed computing systems with associated devices are configured to operate in the distributed network environment, communicating over a suitable data communication network (e.g., the Internet, etc.) and utilizing at least one suitable data communication protocol (e.g., IPX/SPX, X.25, AX.25, AppleTalk™, TCP/IP (e.g., HTTP), etc.). Of note, the embodiments described herein may, of course, be implemented using any appropriate hardware and/or computing software languages. In this regard, those of ordinary skill in the art are well versed in the type of computer hardware that may be used, the type of computer programming techniques that may be used (e.g., object oriented programming), and the type of computer programming languages that may be used (e.g., C++, Objective-C, Swift, Java, Javascript). The aforementioned examples are, of course, illustrative and not restrictive.

The material disclosed herein may be implemented in software or firmware or a combination of them or as instructions stored on a machine-readable medium, which may be read and executed by one or more processors. As used herein, the machine-readable medium may include any medium and/or mechanism for storing or transmitting information in a form readable by a machine (e.g., a computing device). By way of example, and not limitation, the machine-readable medium may comprise computer readable storage media, for tangible or fixed storage of data, or communication media for transient interpretation of code-containing signals. Machine-readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Machine-readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, flash memory storage, or any other physical or material medium which can be used to tangibly store the desired information or data or instructions, including but not limited to electrical, optical, acoustical or other forms of propagated signals (e.g., carrier waves, infrared signals, digital signals, etc.), and which can be accessed by a computer or processor.

In another form, a non-transitory article, such as non-volatile and non-removable computer readable media, may be used with any of the examples mentioned above or other examples except that it does not include a transitory signal per se. It does include those elements other than a signal per se that may hold data temporarily in a "transitory" fashion such as RAM and so forth. In some embodiments, the present invention may rely on one or more distributed and/or centralized databases (e.g., data center).

As used herein, the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

As used herein, a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine-readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

As used herein, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Software may refer to 1) libraries; and/or 2) software that runs over the internet or whose execution occurs within any type of network. Examples of software may include, but are not limited to, software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor.

Rodents intended for use in research and animal testing are housed in vivariums where environmental conditions are carefully monitored to reduce the rodents' exposure to stressors which could potentially impact research outcomes. Gases such as ammonia (NH3) have been identified as an environmental variable which may influence research outcomes and/or negatively impact rodent health. As a reactive and sticky molecule, it easily accumulates to toxic levels. Studies show that prolonged exposure to ammonia of 50 parts per million (ppm) concentration for a 2-week period can cause epithelial degeneration in mice.

A major determinant of ammonia concentrations in vivariums is the frequency of rodent cage changes. Changing cages too frequently can impart undue stress on the rodents, while infrequent cage changes may permit ammonia levels to rise to a point at which they become toxic. Continuous monitoring of ammonia levels in rodent vivariums will allow animal facility technicians to identify the minimal frequency needed for cage changes.

Ammonia is also a major industrial chemical and refrigerant, therefore ammonia monitoring is also conducted in industrial/manufacturing facilities and cold storage facilities to detect leaks, as gaseous ammonia can be toxic at high levels.

In an embodiment, the present invention provides an exemplary inventive automatic and continuous monitoring system and method by building a gas monitoring system using metal oxide sensors. In some embodiments, gasses that could be sensed with the exemplary inventive gas monitoring system and method provided by the present invention include but not limited to ammonia, ethanol, hydrogen sulphide, methane, propane, iso-butane, nitrogen dioxide, and carbon monoxide.

In an embodiment, a metal oxide sensor is made through quantum tunneling techniques, and thus is reusable. In an embodiment, a typical metal oxide sensor has a reduction reaction with ammonia at high temperatures (in a range of about 100° C. to about 400° C.) and an oxidization reaction with oxygen even at room temperature. In an embodiment, the reduction reaction coverts metal oxide to metal, while the oxidization reaction returns the metal back into metal oxide. In an embodiment, the sensor's electrical resistance at the chemical equilibrium state may be measured and the resistance value may be mapped to the corresponding ammonia concentration level.

Some exemplary metal oxide sensors that may be applied in the exemplary inventive gas monitoring system and method, which uses metal-oxides that change their electric resistance in response to gas concentration, include but are not limited to: (1) MICS-5914 (www.sgxsensortech.com) with a typical range of 1-300 ppm and cross sensitive to multiple gasses such as but not limited to ethanol, hydrogen, propane, and iso-butane; (2) TGS2444 (http://www.figarosensor.com) with a typical range of 10-300 ppm and cross sensitive to multiple gasses such as but not limited to ammonia, ethanol, hydrogen sulphide; (3) TGS2611 (http://www.figarosensor.com), sensitive to methane, with a typical range of 500~10,000 ppm and cross sensitive to multiple gasses such as but not limited to hydrogen.

There are several considerations that the exemplary inventive gas monitoring system and method contemplates, which are to make metal oxide sensors suitable for continuous ammonia sensing. First, metal oxide sensors are power hungry and thus they have to maintain a high temperature to keep the reduction reaction going for minutes until a chemical equilibrium is reached. Second, metal oxide sensors have dramatically different sensitivity in terms of their responses to ammonia gas.

To address these considerations, the exemplary inventive gas monitoring system and method implement an accurate prediction model based on Long short-term memory (LSTM) neural networks. The LSTM networks focus on the sensor's transient resistance measurements in a short time window (e.g., a window of 0.2 s) and can accurately predict the final resistance value at the chemical equilibrium state which may take from about two (2) minutes to about thirty (30) minutes to achieve. The exemplary inventive gas monitoring system and method system precisely control the heating power and duration, and accurately measures the ammonia sensor's transient resistance values in ADC samples. Meanwhile, in an embodiment, the exemplary inventive gas monitoring system and method send the ADC samples wirelessly to a remote Raspberry Pi for processing.

Figure 1B:
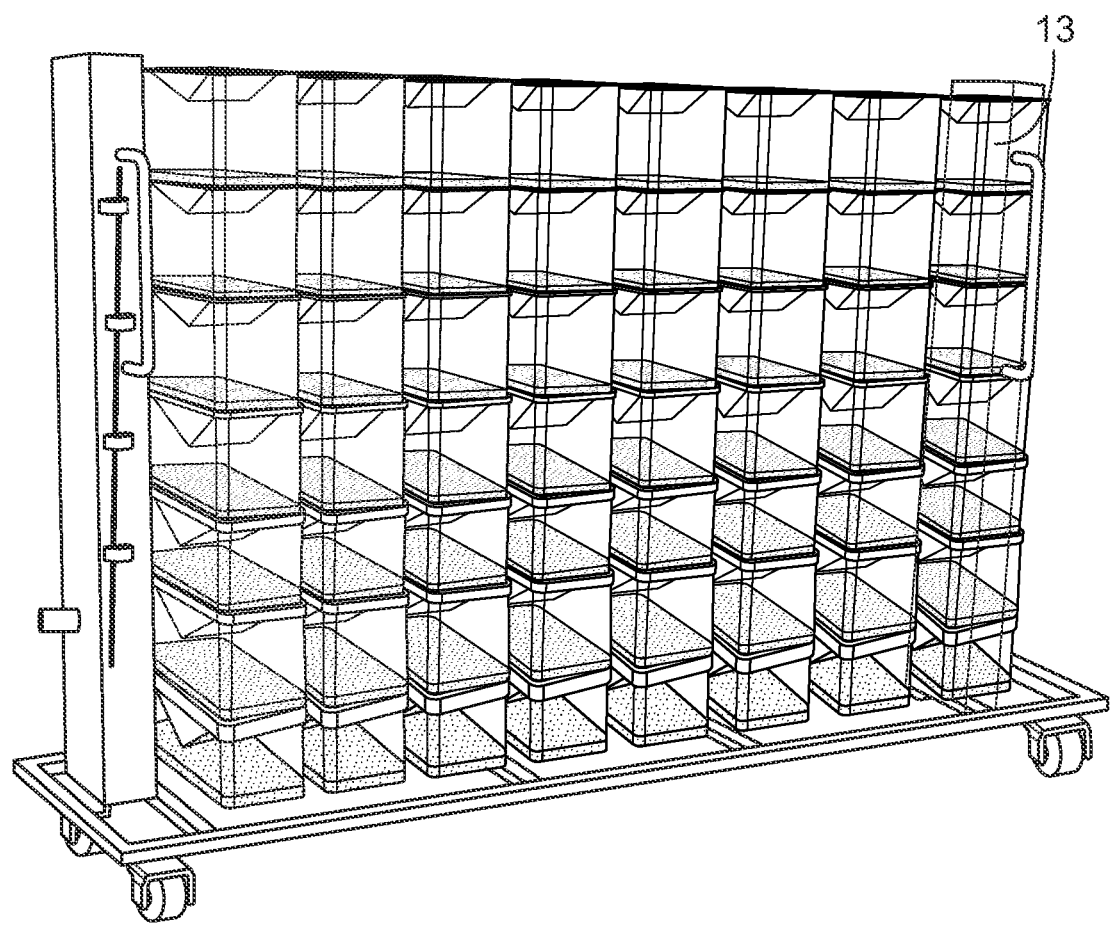

LSTM networks are one type of recurrent neural networks (RNNs), which are developed to deal with the exploding/vanishing gradient problem when training traditional RNNs. By adding the concept of a memory state, LSTM networks can learn the dependencies from time-series data, hence well suited for the present system and method. The LSTM based model as implemented in the exemplary inventive gas monitoring system and method can perform accurate prediction from only a few samples that are collected from a couple of hundreds of milliseconds. Significant power saving can be achieved in this way. In an embodiment, the model as implemented in the exemplary inventive gas monitoring system and method heats the sensor for 0.2 s (during this period, the sensor samples at 40 Hz), which cuts down about 99.6% of the total energy from the usual measurement method that has to heat the sensor for 100 s. In an embodiment, the exemplary inventive gas monitoring system and method can make measurements once every 3 hours for at least 20 years using a single 3.6V Tadiran AA battery. Also, the exemplary inventive gas monitoring system 10 is compact enough to fit into any cage 11 and can support continuous gas monitoring over racks 13 of cages 11, as shown in FIG. 1. Finally, in an embodiment, a wireless design as implemented by the exemplary gas monitoring system and method demands little additional effort to routine cage changes. In other embodiments, the gas monitoring system make employ other suitable forms of communication networks and data transfer systems.

With the exemplary inventive gas monitoring system and method, a home-grown ammonia gas flow system is provided and 13,770 measurements have been conducted using 38 ammonia sensors within a 3-month period. While conducting measurements, the exemplary inventive gas monitoring system and method have varied the ammonia concentration from 0 ppm to 240 ppm. The model as implemented by the exemplary inventive gas monitoring system and method proves to be precise: across different ammonia concentrations, the average prediction error rate for the equilibrium state resistance ADC value is 0.12% and the average absolute estimation error for the ammonia concentration is 9.38 ppm. Also, the model as implemented by the exemplary inventive gas monitoring system and method may be trained using one sensor's data and tested using data from other sensors, and still achieve equally accurate prediction results.

The exemplary inventive gas monitoring system and method are deployed into two animal research labs with a total of 38 rodent cages and completed a 4-month trial at the National Institutes of Health (NIH) and a second 3-month breeding-related trial at Cornell University. The trials demonstrate that the exemplary inventive gas monitoring system and method offers a viable solution for accurate and continuous gas monitoring such as ammonia monitoring for large-scale laboratory animal facilities. The observed ammonia level changes accurately reflect the cage change events logged by the facility staff. Finally, the ammonia sensing system can be readily used in other application areas that require ammonia sensing, including air quality in other animal care locations, such as stables, and ammonia leak detection in industrial and factory settings.

The main features provided by the exemplary inventive gas monitoring system and method include but not limited to: providing a low-power, automatic, accurate and wireless ammonia monitoring system, which easily fits into any rodent cage and can last for 20 years with a single Tadiran AA battery.

Other features of the exemplary gas monitoring system and method include developing a prediction model based on LSTM neural networks that accurately estimated the equilibrium state resistance value given a few transient resistance samples collected within the first 0.2 s. The exemplary inventive gas monitoring system and method show two orders of magnitude reduction in energy consumption of metal oxide sensor-based ammonia measurement.

Additional features of the exemplary gas monitoring system and method includes providing a home-grown ammonia gas flow system and conducted many measurements over long time periods. Such systems may be partnered with cage manufacturers and deployed the system into two animal research laboratories and completed two field trials.

Metal Oxide Based Ammonia Monitoring

In an embodiment, a metal oxide sensor is a reusable sensor for measuring a concentration level surrounding the sensor. In a temperature range of about 100° C. to about 400° C., it leads to a reduction reaction with combustible gases such as ammonia. This type of reaction converts metal oxide to metal that has much smaller electrical resistance. Meanwhile, metal may have an oxidation reaction by absorbing oxygen on the surface and forms metal oxide, even at room temperature. As a result, by measuring how the electrical resistance changes, the ammonia level may be inferred.

Figure 2:
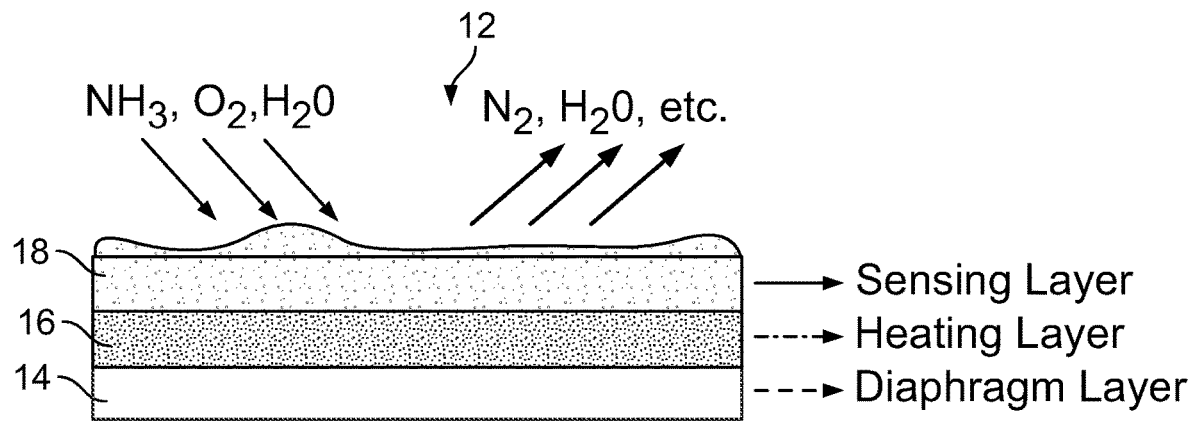
FIG. 2 shows an embodiment of a metal oxide sensor.
Figure 3:
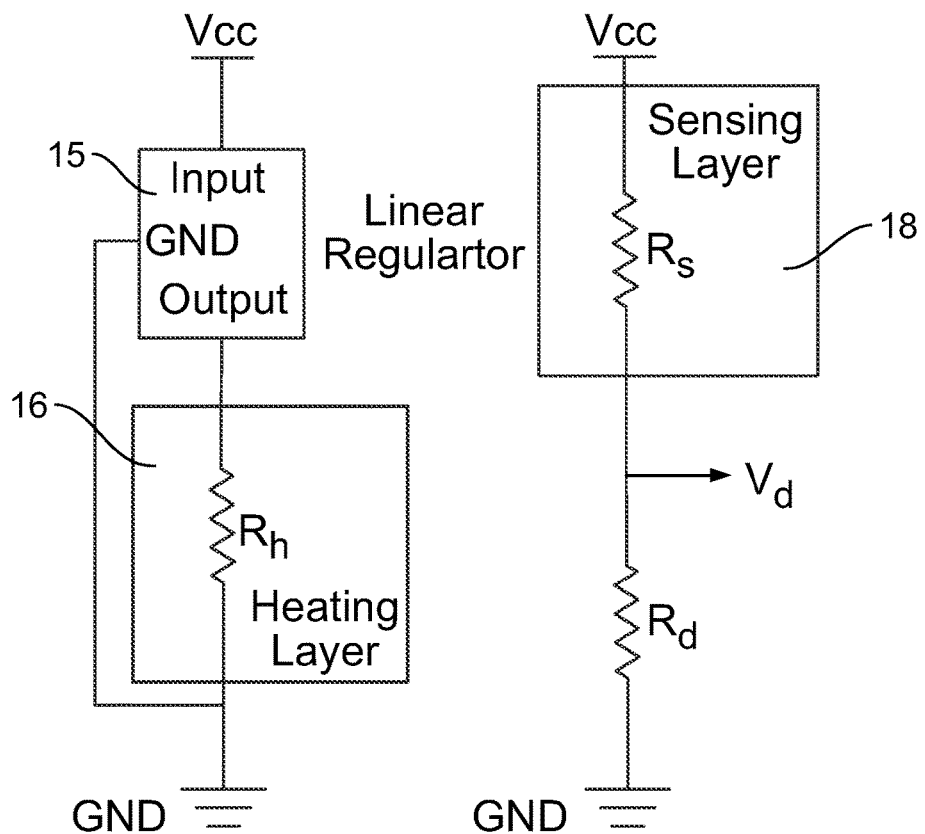
FIG. 3 shows and embodiment of a sensor circuit design.

FIG. 2 shows a sensor 12 as applied in the exemplary inventive gas monitoring system and method that consists of three layers from bottom to top: a machined diaphragm base layer 14, an embedded heating layer 16 and a sensing layer 18. When making a measurement, the exemplary inventive gas monitoring system and method first heat the sensor 12 to a temperature in a range of about 100° C. to about 400° C. Next, the exemplary inventive gas monitoring system and method keep the temperature constant, let metal oxide on the sensing layer 18 have reduction-oxidation reaction (redox) with ammonia and oxygen simultaneously, and wait until the redox process reaches its chemical equilibrium. When the chemical equilibrium is reached, the rate of the metal oxide being reduced by ammonia is equal to the rate of the metal being oxidized by oxygen. Finally, the exemplary inventive gas monitoring system and method measure the resistance of the sensing layer 18 through a 10-bit ADC on a microprocessor 15 and converts the ADC sample to the corresponding ammonia concentration, as shown in FIG. 3. The entire measurement is rather time-consuming as it might take a few minutes to reach the chemical equilibrium. Keeping the sensor's temperature steady in a range of about 100° C. to about 400° C. for this period of time can be quite power consuming.

Transient-Predict

The exemplary inventive gas monitoring system and method are based on a metal oxide sensor. By implementing the low-power design, the exemplary inventive gas monitoring system is compact and can be easily put into a regular rodent cage. The system automatically measures the gas, e.g., ammonia, concentration inside the cage without any additional human effort. The salient features of the exemplary inventive gas monitoring system is described herein below.

Low Power Ammonia Measurement: In an embodiment, the metal oxide sensor demands a temperature in a range of about 100° C. to about 400° C. over a few minutes in order to trigger and keep the reduction reaction. This may consume a significant amount of power. In fact, heating alone costs more than 99% of the total amount of energy for a 100-second heating period on average. This is a reason why the current metal oxide ammonia measurement tools operate on large batteries and are usually hand-held devices.

The exemplary inventive gas monitoring system and method address this challenge by significantly reducing the amount of energy required for each measurement. One of the main contributions is to design a prediction model which can greatly shorten the time required for measurement. The exemplary inventive gas monitoring system and method take the transient ADC samples collected in the first 0.2 s and can accurately predict the ADC measurement in a few minutes, which is referred to as Transient-Predict. Transient-Predict consumes much less power and requires a much smaller battery, so it can be made compact enough to fit into a standard cage and provide continuous wireless monitoring for years, as shown in FIG. 1(a).

Accurate Prediction of the Equilibrium Resistance: It is a challenge to predict the ADC value in the equilibrium state (which usually takes a few minutes to arrive at) from the first few transient ADC samples collected in less than a second. This challenge is made even harder by the fact that each metal oxide sensor has drastically different characteristics. Metal oxide sensors are made by the quantum tunneling technique and the growth of metal oxide on the sensing layer is hard to control. As such, the sensitivity of the sensors varies, sometimes by a factor of 10.

Further, the process of reaching the chemical equilibrium is impacted by several factors: the initial state of the sensing layer (such as the percentage of metal in the form of metal oxide and the amount of ammonia stuck to the surface), ammonia concentration in the air, oxygen concentration, humidity level, heating temperature, ambient temperature, etc. Considering these factors one by one in a prediction model can be an onerous task as each factor is non-linear with respect to the ammonia concentration level.

The exemplary inventive gas monitoring system and method solve this challenge by developing suitable LSTM neural networks to learn the relationship between transient ADC values and the final equilibrium state value. The design detail is described in "Design of Transient-Predict" section.

Prototyping and Power Consumption Profiling of Transient-Predict

Among the 38 prototype ammonia sensors, in one embodiment, the exemplary inventive gas monitoring system and method integrate an SGX Sensortech MiCS-5914 metal oxide sensor with a general-purpose embedded platform that has a Texas Instrument (TI) MSP430 microcontroller with a 10-bit ADC and a TI CC1100 radio transceiver module.

Figure 4:
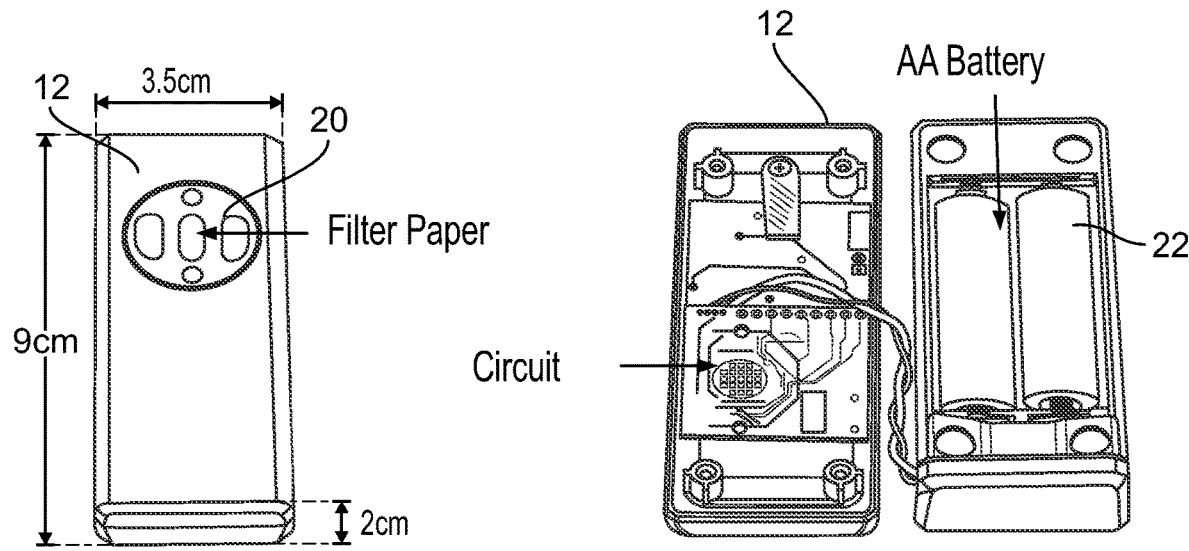
FIG. 4 shows a gas sensor.
Figure 5:
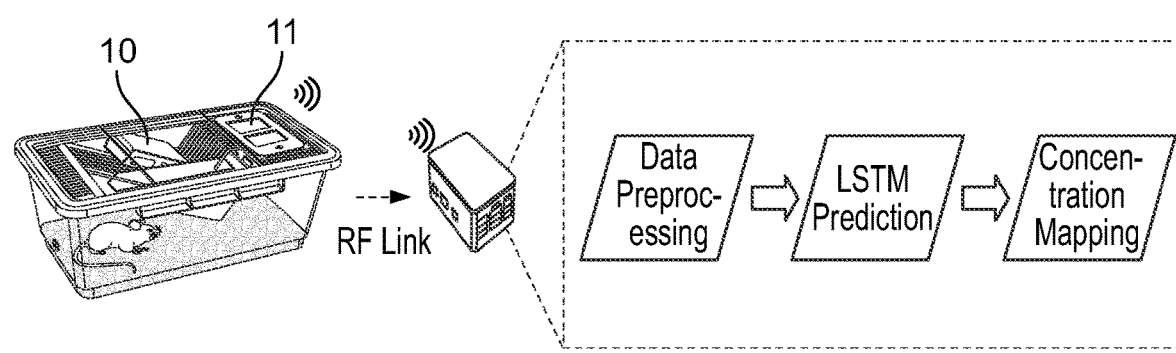
FIG. 5 shows an overview of a Transient-Predict.

FIG. 4 shows an embodiment of the dimensions of the sensor 12 as implemented by the exemplary inventive gas monitoring system and method is 9 cm by 3.5 cm by 2 cm according to some embodiments. The sensor is protected with a filter paper 20 and powered by two AA lithium batteries 22. The sensor measures the electrical resistance value through ADC, and the ADC samples are wirelessly transmitted to a receiver that is connected to a Raspberry Pi or a computer for subsequent processing. In an embodiment, a final processing of the exemplary inventive gas monitoring system and method mainly consists of three steps: (1) preprocessing, (2) predicting the equilibrium resistance ADC value using a few transit resistance ADC values, and (3) converting the predicted equilibrium resistance value to the corresponding ammonia concentration level. An overview of our Transient-Predict system is shown in FIG. 5.

Dominance of ammonia in a rodent cage: In an embodiment, the metal oxide sensors are reactive to some gases (i.e., ammonia, ethanol and hydrogen) at low concentration (starting around 1 ppm) and other gases (i.e., propane and iso-butane) at high concentration (above 1000 ppm). Considering the environment inside a rodent cage, the reaction between ammonia and the sensor dominates overall sensor reading, as the concentrations of other reactive gases are much lower than ammonia.

Energy Profiling: The power consumption of the sensor (e.g., ammonia sensor) in both the sleep stage and the measurement stage are described herein. The exemplary inventive gas monitoring system and method mount a fixed resistor in series with the sensor and a direct current (DC) power supply, and use the voltage drop across the fixed resistor to infer the power consumption of the sensor. In an embodiment, profile results of the exemplary inventive gas monitoring system and the traditional minutes heating approach in Table 1, which illustrates the power consumption profiling for the inventive exemplary Transient-Predict system. In an embodiment, the system consumes 0.64 A during sleep and 30,700 A for a measurement. Compared to the traditional minutes heating approach, the exemplary inventive gas monitoring system saves about 99.6% of energy. On average, the exemplary inventive gas monitoring system can last for at least 20 years with one Tadiran AA lithium battery (2400 mAh), assuming it makes one measurement in every 3 hours.

TABLE 1

| Stage | Power (A) | Time (s) |
|---|---|---|
| Sleep | 0.64 | 10,799.8 |
| Measurement | 30,700 | 0.2 |
| Avg Power Consumption | | 0.0012 mA |

In an embodiment, after sleeping for 3 hours, the sensor wakes up for 0.2 s. During the measurement period, the sensor heats up, takes ADC samples at 40 Hz, and transmits the samples to the receiver. After 0.2 s, the sensor goes back to sleep. In an embodiment, the exemplary inventive gas monitoring system consumes 0.64 A during the sleep stage and about 30.7 mA for each measurement. As a result, the exemplary inventive gas monitoring system saves 99.6% of energy compared to the traditional approach and can last for at least 20 years with a Tadiran AA battery, assuming it makes one measurement in every 3 hours.

Design of Transient-Predict

An embodiment of the detailed design of Transient-Predict is described herein, which is centered around predicting the equilibrium resistance value using a few transient resistance values through LSTM neural networks.

In an embodiment, the baseline ammonia sensing approach involves heating the metal oxide sensor for a period from about two (2) minutes to about thirty (30) minutes such that the chemical reaction on the sensor reaches the equilibrium. The main drawback of this approach is the high energy requirement in heating the sensor. On the contrary, in an embodiment, Transient-Predict only needs to heat the sensor for a very short duration, such as up to 200 milliseconds, or, in other embodiments, up to one (1) second. During this duration, the exemplary inventive gas monitoring system and method sample the transient ADC values. Then the exemplary inventive gas monitoring system and method predict the final ADC value in the chemical equilibrium state based upon these transient responses. Considering that the exemplary inventive gas monitoring system and method only need to heat the sensor for a up to 200 milliseconds, or, in other embodiments, up to one (1) second, instead of a few minutes, the exemplary inventive gas monitoring system and method can reduce more than 99% of the overall energy consumption. At the heart of the Transient-Predict approach lies in an accurate prediction algorithm that can quickly learn how the transient ADC values map to the final equilibrium ADC value.

In an embodiment, the data collection works as implemented by the exemplary inventive gas monitoring system and method is as follows. First, a sensor wakes up from sleep and turns on the heater inside of the sensor. For the first second, the sensor measures its ADC samples at 40 Hz. During this 1-second period, the ADC values have significant variations due to the drastic reduction-oxidation reaction, and the samples collected in this period are thus referred to as transient responses. Then, the sensor turns o the heater and goes back to sleep for 3 hours till the next duty cycle. Note in order to collect the ground truth, the system heats the sensor and measures the final ADC sample at 100 s when the expected chemical equilibrium has occurred. In total, 41 samples have been collected for each experiment. The objective is to find and train a model that can predict the final ADC sample based upon as few transient samples as possible.

Figure 6A:
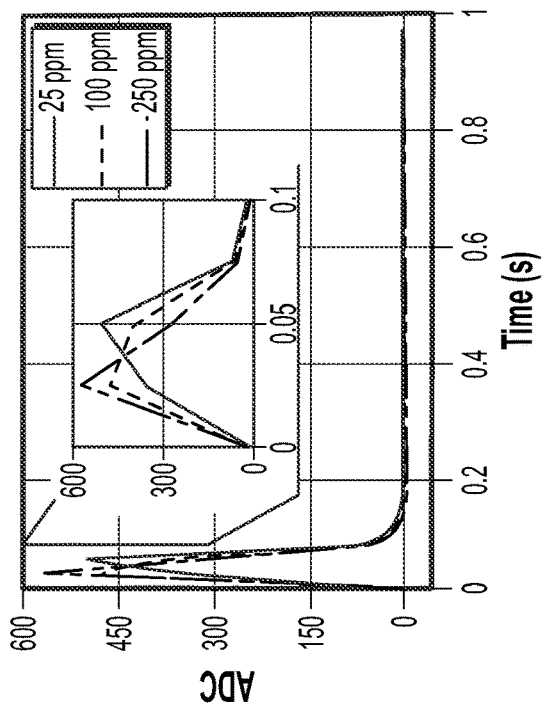
FIG. 6(a) shows a 100-second ADC trace until the chemical equilibrium is reached, with a first shade that marks the 1-second transient period worked with in Transient-Predict.
Figure 6B:
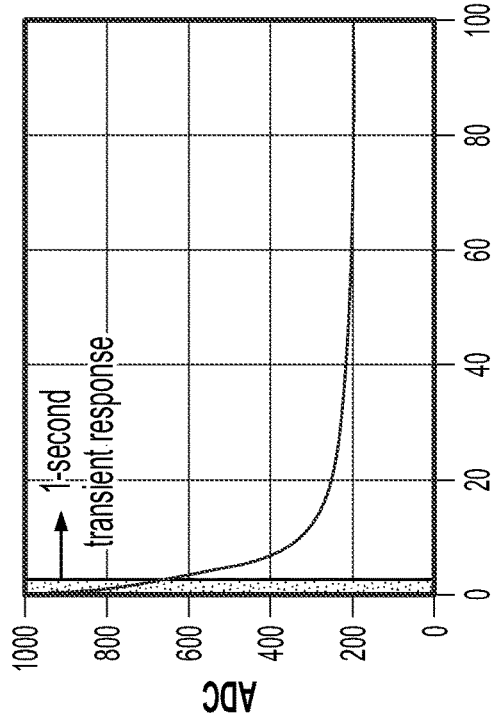
FIG. 6(b) shows a sensor's 1-second transient ADC samples under ammonia concentration of 25, 100, 200 ppm.

FIG. 6(a) shows an example of ADC values traced in a 100-second period (the chemical equilibrium is reached by the end). On the same plot, the 1-second transient period is also marked working with in Transient-Predict. More example transient ADC traces are shown in FIG. 6(b).

Step I: Data Preprocessing

Since the exemplary inventive gas monitoring system and method transmit transient ADC values wirelessly, a small fraction of the data may become missing or polluted due to collision. To address this problem, the exemplary inventive gas monitoring system and method apply the following preprocessing steps.

First, in an embodiment, the exemplary inventive gas monitoring system and method ignore measurements that do not have the first 5 ADC samples or the final sample. The first few samples are critically important for training our prediction model, and the exemplary inventive gas monitoring system and method use the final sample as the ground truth for evaluating the prediction model.

Second, the exemplary inventive gas monitoring system and method apply the spline interpolation technique on the samples such that the missing data is recovered. After the interpolation, the exemplary inventive gas monitoring system and method have 41 samples for each measurement: the first 40 samples are measured within the first second during the measurement and the last sample is measured at 100 s when the chemical equilibrium is reached.

Step II: Equilibrium State Electrical Resistance Prediction

The long short-term memory (LSTM) neural networks are one type of recurrent neural networks (RNNs). While common RNNs suffer from failing to learn information dependencies over a large time period, LSTM networks overcome this shortcoming by keeping the memory in a unit called the cell state and maintaining the cell state through a dynamic gating mechanism.

Figure 7:
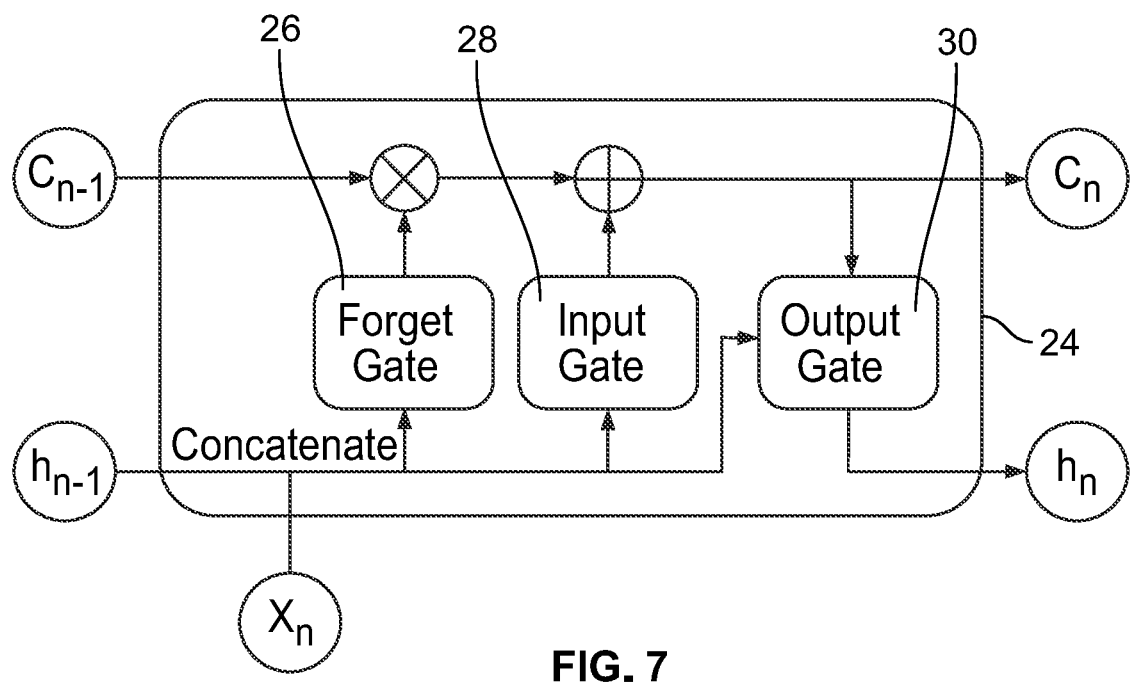
FIG. 7 shows an n-th LSTM layer.

In fact, common LSTM networks have multiple sequential LSTM blocks 24 where each block consists of three gates: a forget gate 26, an input gate 28 and an output gate 30. The architecture of an LSTM block 24 is shown in FIG. 7. The forget gate 26 in the n-th LSTM block 24 uses the input $x_n$ at time n and the previous block's 24 output $h_{n-1}$ to maintain the relevant memory and forget the irrelevant memory. The input gate 28 updates the memory in the current cell state $C_n$ based on the partial memory provided by the forget gate 26, the input $x_n$ and the previous output $h_{n-1}$. Later, combining $x_n$, $h_{n-1}$, and the new memory, the output gate 30 computes the new output $h_n$.

Figure 8:
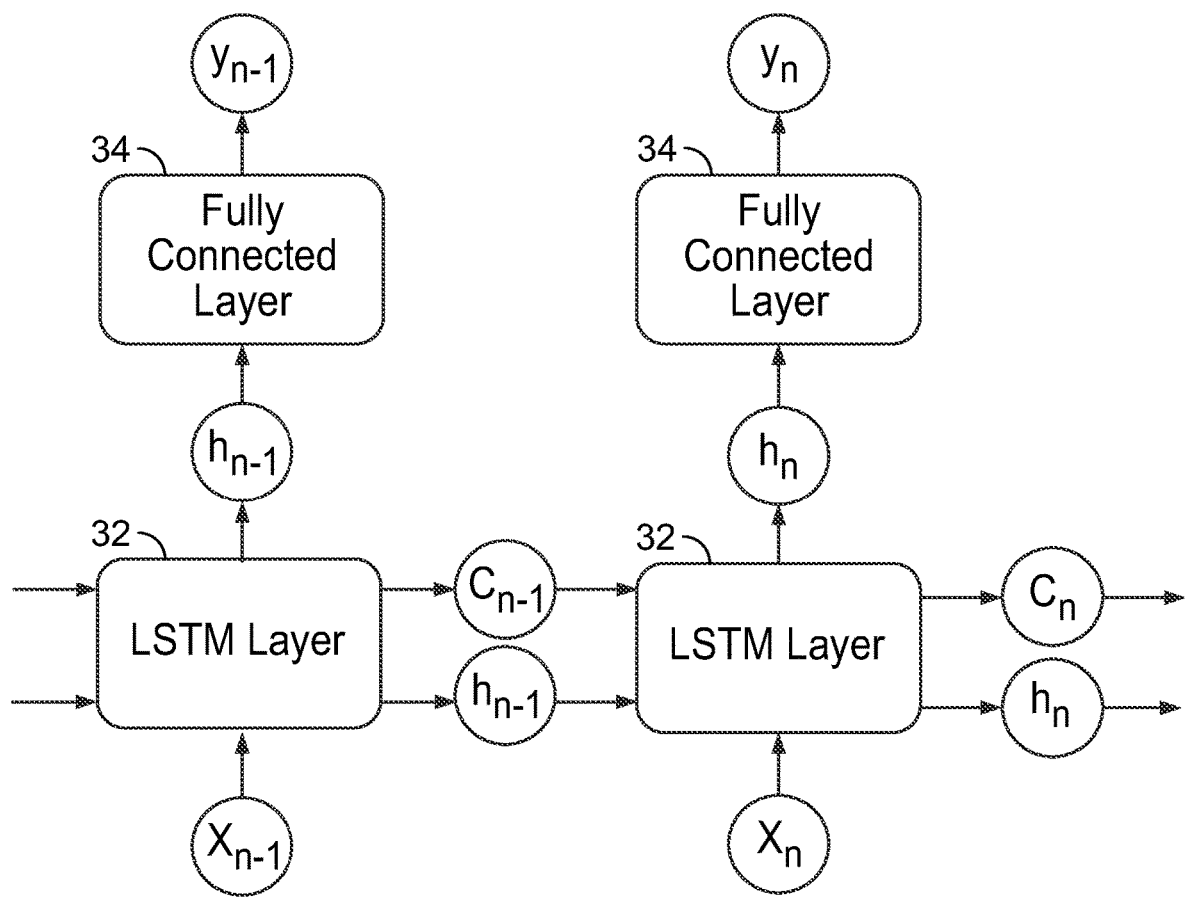
FIG. 8 shows an LSTM neural network structure with each vertical column shown constituting a block of the LSTM neural networks.

The LSTM neural networks as implemented by the exemplary inventive gas monitoring system and method consist of two layers: an LSTM layer 32 followed by a fully connected layer 34, as shown in the vertical pipeline 36 in FIG. 8. The LSTM layer 32 at time n processes the input data $x_n$, together with the cell state $c_{n-1}$ and the previous output $h_{n-1}$, and sends the output $h_n$ to a fully connected layer 34. The fully connected layer 34 generates the final output for the entire network. Table 2 shows the summary representation of a well-tuned network structure. The exemplary inventive gas monitoring system and method build and train the networks with Keras, a deep learning framework based on python. In an embodiment, the model is trained with the mean squared error as the objective loss function and all the coefficients are optimized by the Adam algorithm. Initially, the exemplary inventive gas monitoring system and method set the batch size to 10 and the number of hidden neurons to 500. It is noted that the number of hidden neurons is correlated with the input window size. The exemplary inventive gas monitoring system and method start with sufficient hidden neurons for a large window size and further tune parameters (i.e., the window size, the batch size and the number of hidden neurons) and report their impact on the performance. Table 2 shows the final structure of an embodiment of the LSTM neural networks, in which the batch size is set to 2 and the number of neurons is set to 75.

TABLE 2

| Layer | Output Shape | # of Parameters |
| --- | --- | --- |
| LSTM | (2, 75) | 23,100 |
| Fully Connected | (2, 1) | 76 |

Preparing the Transient ADC Samples for LSTM Networks

The exemplary inventive gas monitoring system and method prepare the transient ADC samples (after the pre-processing step) to make them suitable for the LSTM networks. The following two techniques may be used in the exemplary inventive gas monitoring system and method according to some embodiments.

First, the exemplary inventive gas monitoring system and method use the first derivatives of the ADC samples, instead of the samples themselves. For the i-th sample s(i) in a measurement, the first derivative is computed as $$d_1(i) = s(i) - s(i-1). \quad (1)$$

The use of first derivatives greatly helps the LSTM neural networks learn the desired patterns from the data. It is observed that the number of epochs required for training the neural networks significantly decreases when the networks are fed with the derivatives rather than the raw data. Specifically, with the raw ADC samples, the training loss starts quite large from the first epoch and remains high for the subsequent 100 epochs, while with the derivatives, the networks quickly converge to a reasonable local minimum within 30 epochs. The reason is that the equilibrium ADC value is strongly correlated with how the previous samples change, and the derivatives reflect such changes more directly.

Figure 6C:
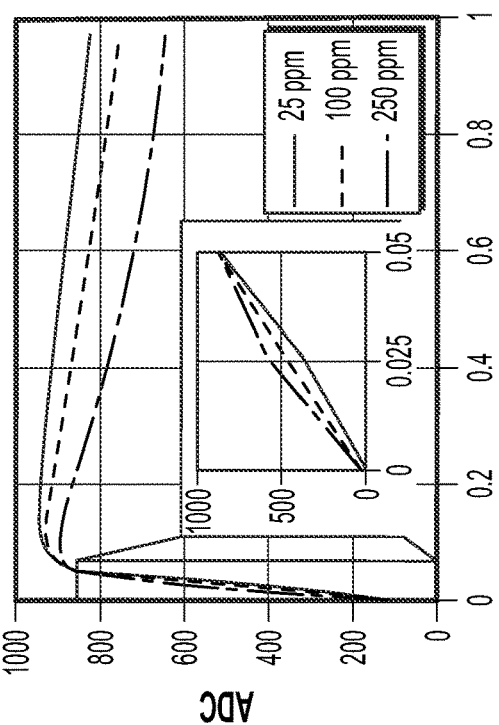
FIG. 6(c) shows a first derivatives of the same transient samples as in FIG. 6(b), with each derivative curve having two parts: between 0-0.1 s, the derivatives are positive with large variations, and after 0.1 s, the derivatives are negative but stable.

FIGS. 6(b) and 6(c) show three transient ADC traces and their corresponding derivatives under ammonia concentration of 25, 100, and 200 ppm. Measurements in the first 0.2 s show larger variations and thus contains more information. Also, the ADC samples decrease between 0.2 s and 1 s, and the decreasing rate is quite consistent. By calculating the derivatives, the exemplary inventive gas monitoring system and method make these patterns more explicit to the LSTM model, which then significantly improves its performance.

Secondly, the exemplary inventive gas monitoring system and method scale the derivative d1(i) to the range of [a, b] by $$S(i) = \frac{d_1(i) - \min(d_1)}{\max(d_1) - \min(d_1)} (b - a) + a. \quad (2)$$

In some embodiments, the exemplary inventive gas monitoring system and method pick [−1, 1] as the specific range. This step can significantly bring down the training error from 10 to 40 (such 20 or 30) to below $1*10^{-3}$. Here, the exemplary inventive gas monitoring system and method mainly consider sigmoid function and tanh function, both of which are commonly used in neural networks. The scaling step of the exemplary inventive gas monitoring method transforms the data into the desired ranges for both functions. For example, the output of the tanh function will exhibit more pronounced changes when the input data are scaled between −1 and 1. As such, the layer outputs become more distinguishable, rending it easier to reduce the objective loss.

Step III: Ammonia Concentration Calibration

Figure 9:
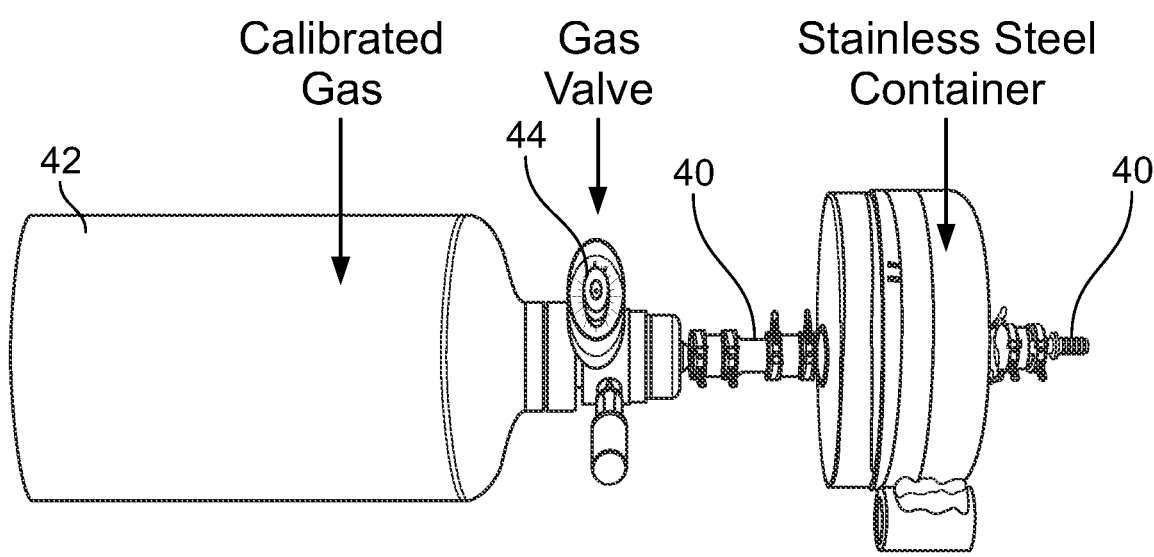
FIG. 9 shows an ADC to concentration mapping system involving industrial calibrated gas, including a gas valve with flow rate control, and a stainless-steel container.

In this last step, the exemplary inventive gas monitoring system and method map the estimated equilibrium ADC value to the corresponding ammonia concentration level. In some embodiments, the exemplary inventive gas monitoring system and method place multiple sensors into a stainless-steel container 38 with fresh air. As shown in FIG. 9, the container 38 has one gas connector 40 on each side and has high corrosive resistance to ammonia. Next, the exemplary inventive gas monitoring system and method connect one of the connectors 40 to a valve controlled cylinder 42 having a gas valve 44, which contains calibrated ammonia, while leaving the other connector 40 to the open air. Then, the exemplary inventive gas monitoring system and method continuously release calibrated ammonia gas. After some time, the gas in the container 38 reaches the same ammonia concentration inside of the calibrated ammonia cylinder 42 due to the mechanical equilibrium effect.

The exemplary inventive gas monitoring system and method repeat this process with different ammonia concentration levels and fit the data into a curve-fitting model. Although the manufacturer suggests a polynomial model, a power law curve-fitting model fits the data better. The power law model is defined as:

$$C = a\left(\frac{1}{R_s}\right)^n, \quad (3)$$

where C is the concentration, a is a constant prefactor, n is a constant exponent, and Rs is calculated as $$R_s = \frac{V_{cc} - V_d}{V_d} R_d, \quad (4)$$

based on the circuit shown in FIG. 3. The exemplary inventive gas monitoring system and method can solve Equation 3 by taking the log on both sides and treat it as a linear least curve fitting problem.

Evaluation of Transient-Predict

In some embodiments, an error rate is reported in predicting the equilibrium ADC value as well as the estimation error in mapping an ADC value to the corresponding ammonia concentration level.

Evaluation of the LSTM Based Equilibrium ADC Value Prediction

The exemplary inventive gas monitoring system and method first evaluate how well our LSTM neural networks model predicts the equilibrium ADC value.

Figure 10:
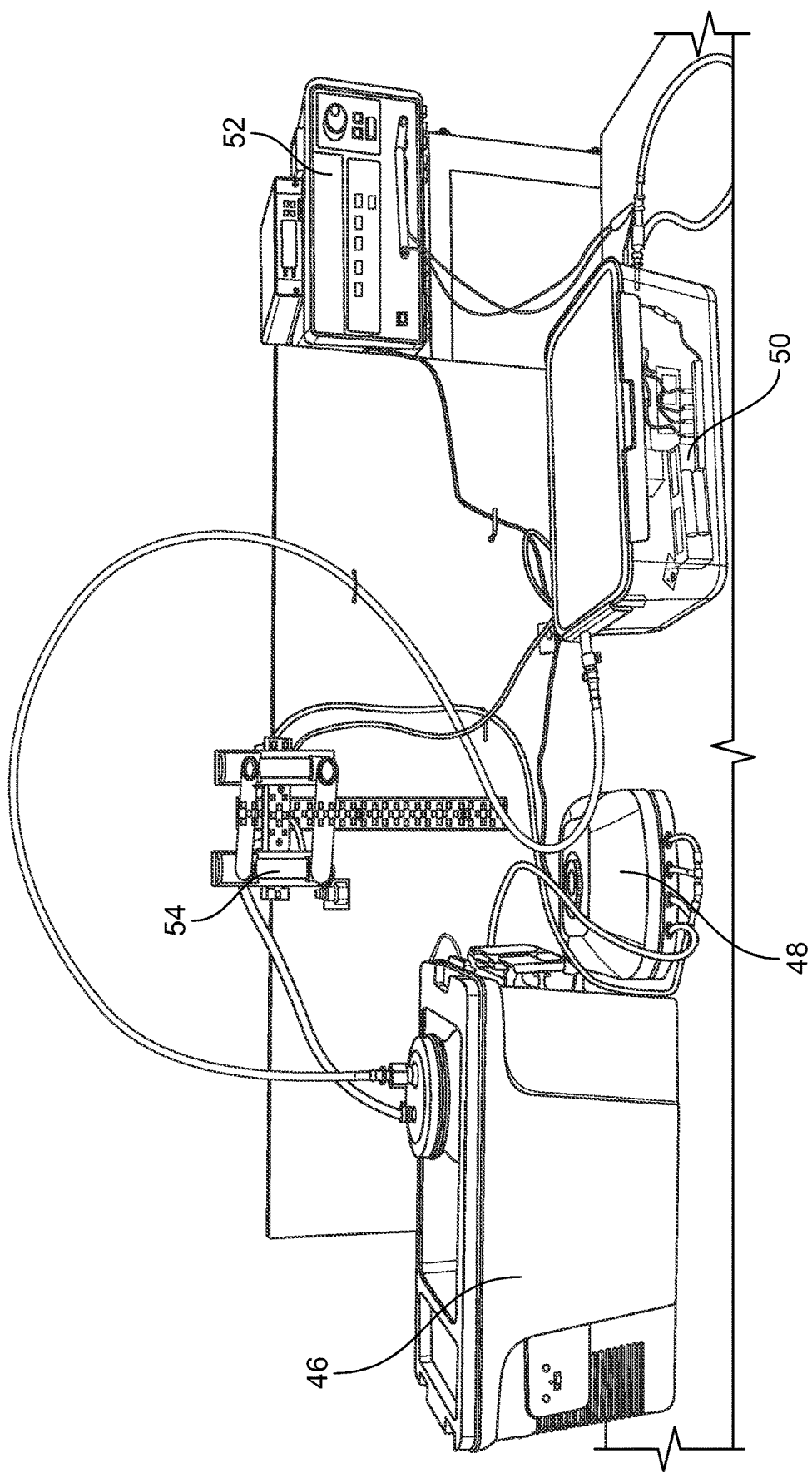
FIG. 10 shows a gas flow system.

Experimental Setting. In an embodiment, a gas flow system is built which consists of a gas washing bottle 46, an anti-corrosive air pump 48, an anti-corrosive container 50, a power supply 52, flow meters 54 and other parts (e.g., Teflon tubes, stainless steel connectors, etc.), as shown in FIG. 10. The air pump 48 generates the directional air flow that goes through the gas washing bottle 46 to the container 50. The exemplary inventive gas monitoring system and method can switch between the self-circulation mode and no-circulation mode by connecting/disconnecting the outlet of the container 50 to the inlet of the air pump 48. The gas washing bottle 46 contains a mixture of water-based ammonia hydroxide and distilled water, serving as the source of ammonia gas. The exemplary inventive gas monitoring system and method can manipulate the ammonia gas concentration by tuning the ratio of the liquid mixture. Inside the container 50 are a spinning fan and multiple ammonia sensors. The container 50 works as a buffer of ammonia gas and the fan can speed up the uniform balance of ammonia gas and air. In some embodiments, all the equipment parts are washed with the distilled water and then baked at an appropriate temperature for at least 24 hours, in order to eliminate any gas which may affect the measurements.

Over a period of 3 months, data is collected from a total of 38 sensors. All the sensors were placed into the anti-corrosive container 50 for a period between 28 and 60 days. During this 3-month period, the exemplary inventive gas monitoring system and method collected a total of 13,770 measurements. To conduct the controlled experiments, the exemplary inventive gas monitoring system and method repeatedly performed different combinations of the following operations: (1) injecting distilled water in the container 50 and collecting data; (2) injecting the mixture of water-based ammonia hydroxide and distilled water in a self-circulation mode and measuring the concentration drift over time; (3) injecting more ammonia hydroxide to increase the ammonia concentration in the container 50; (4) switching to a no-circulation mode and measuring the ammonia decay over time; (5) cleaning the gas washing bottle 46 with distilled water and blowing fresh air into the container 50.

The Impact of the LSTM Neural Networks Parameters. The performance of the LSTM neural networks has a significant bearing on the overall performance of Transient-Predict. Specifically, the exemplary inventive gas monitoring system and method consider the following non-limiting parameters that can impact the performance of the LSTM neural networks: the transient window size, the batch size, the number of hidden neurons, and whether to have a stateful or stateless LSTM neural networks. Empirically, the exemplary inventive gas monitoring system and method set the max number of epochs as 100 and allow an early termination of the training phase when the training loss becomes below $1*10^{-4}$. Also, the exemplary inventive gas monitoring system and method use a learning rate of 0.1 in the following evaluation.

Figure 11:
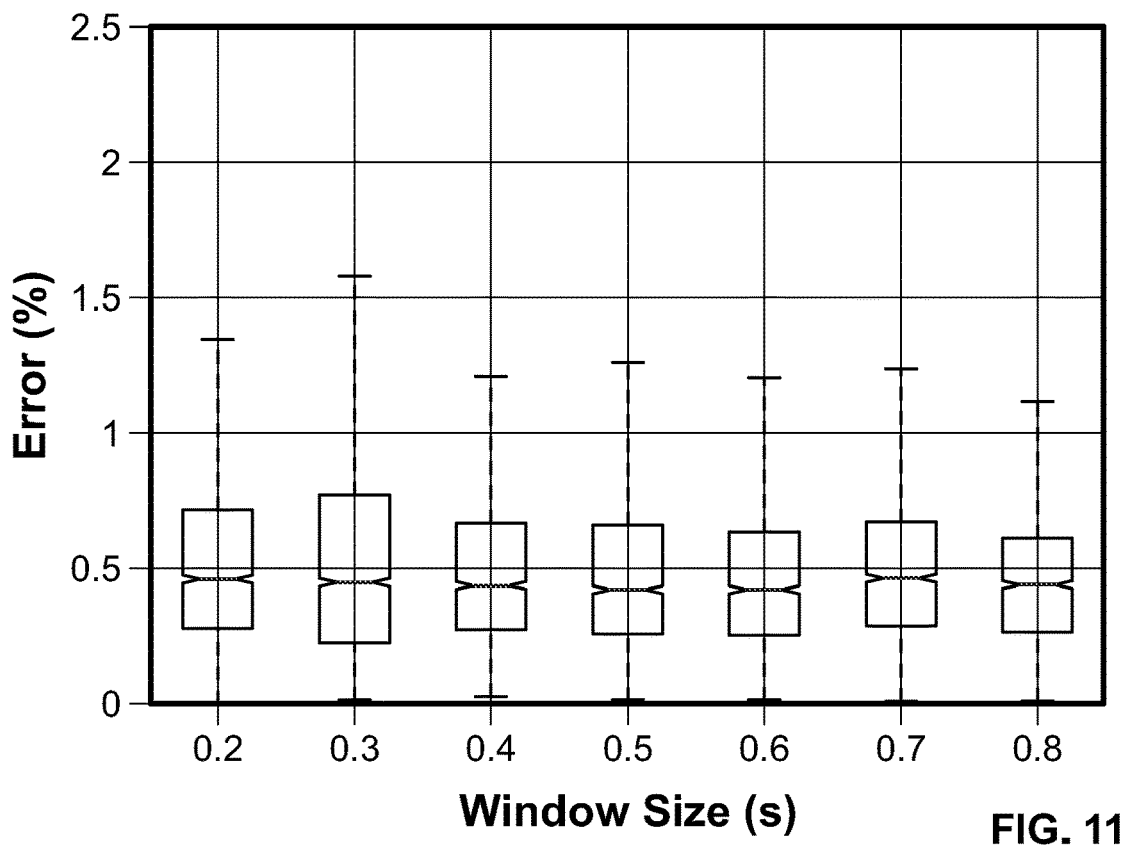
FIG. 11 shows a graph of window size (s) versus error percentage (%) involving a gas system involving varying the transient window size from 0.2 s to 0.8 s and reporting the resultant prediction error rate the ratio between the absolute prediction error and the ground truth.

Transient window size: In Transient-Predict, the exemplary inventive gas monitoring system and method use the transient ADC samples collected from the transient window size to predict the equilibrium ADC value. The window size thus has a significant impact on the overall performance. Here, the exemplary inventive gas monitoring system and method program the sensor to sample at 40 Hz for the first 1 second. In addition, it also collects the equilibrium ADC sample at the 100-th second. The exemplary inventive gas monitoring system and method vary the transient window size from 0.2 s to 0.8 s and report the resultant prediction error rate the ratio between the absolute prediction error and the ground truth in FIG. 11.

In some embodiments, any window size larger than or equal to 0.2 s is sufficient for training and yields accurate results. When the transient window size is 0.2 s or longer, the average prediction error rate is 0.94% or lower; when the transient window size is 0.1 s, the average prediction error rate is 50%. The reason is that the most important information is embedded in the first few transient ADC samples there are 8 samples for a 0.2 s window. Capturing these few samples is the key to our LSTM model. As such, in the rest of the description, the window size is fixed to 0.2 s. In an embodiment, a transient window size ranges from 0.2 s to 0.8 s and the average error rate is reported. In an embodiment, the transient window size of 0.6 s gives the lowest average error rate at 0.89%. In another embodiment, a window size of 0.2 s yields an average error rate at 0.94%.

Figure 12:
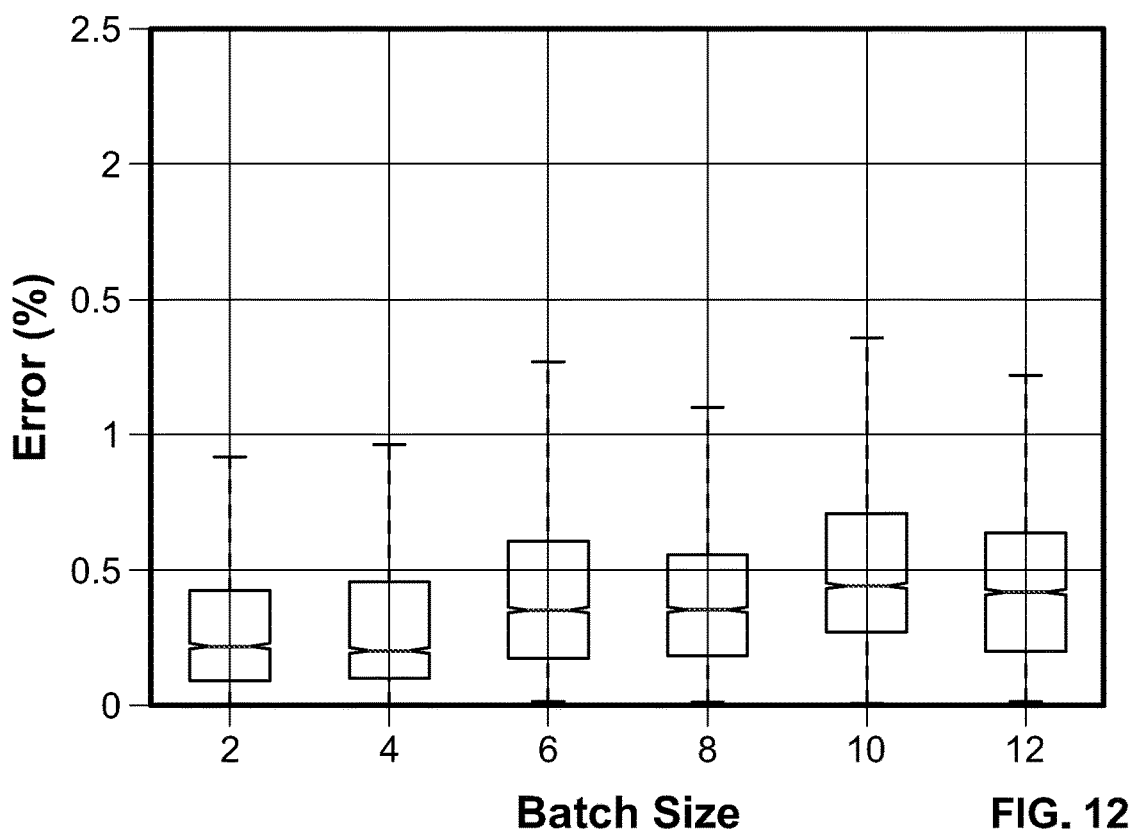
FIG. 12 shows a graph of batch size versus error percentage (%) involving varying the batch size from 2 to 12 and reporting the average error rate.

Batch size: The batch size denes the number of samples that go to forward propagation through the LSTM networks before a backward propagation occurs. An optimal batch size is a good representation of the data set and can prevent models from overfitting. The exemplary inventive gas monitoring system and method may vary the batch size from 2 to 12 and report the resultant average error rate in FIG. 12. In some embodiments, a batch size of 2 is optimal with an average error rate of 0.42%. Larger batch sizes lead to slightly higher error rates (even though the overall error rates are very low). Meanwhile, a batch size of 1 leads to an unstable training process a small fraction of the models work well while the majority of the models have much larger errors. As such, in the rest of the description, the batch size is fixed to 2.

Figure 13:
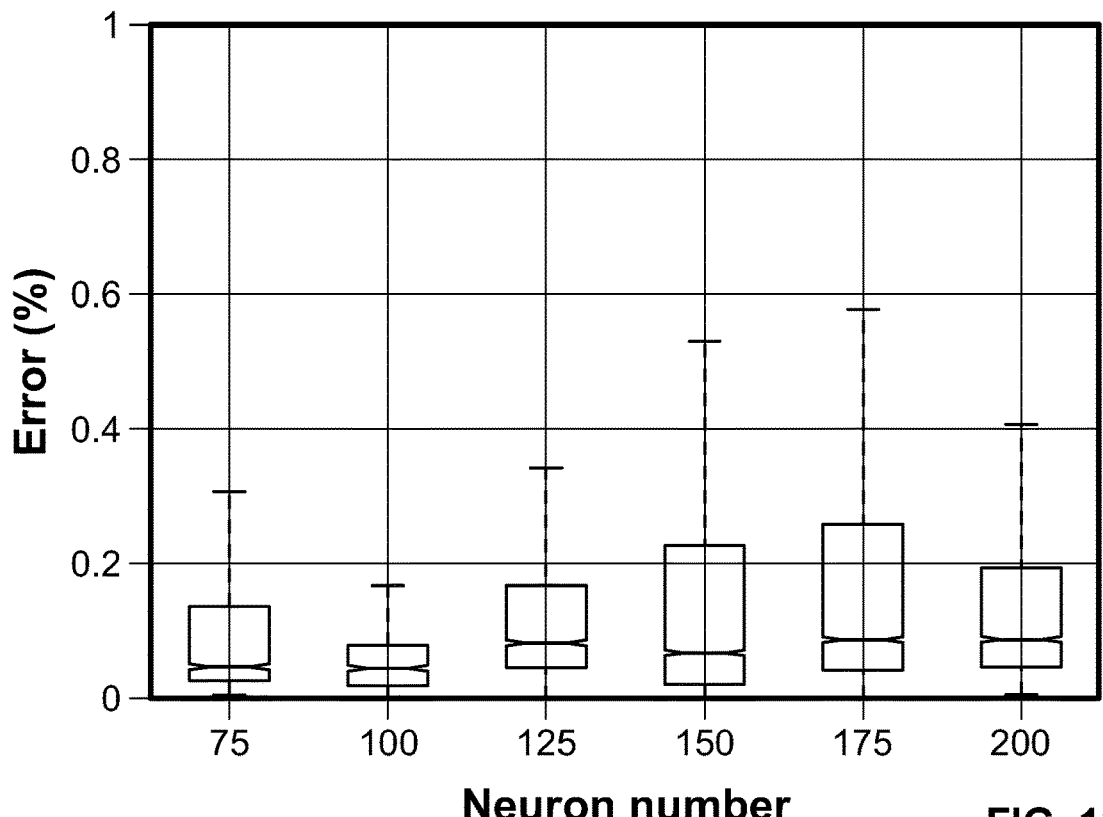
FIG. 13 shows a graph of neuron number versus error percentage (%) involving varying a number of hidden neurons from 200 to 75 and reporting the average error rate.

Number of hidden neurons: The number of hidden neurons is another important parameter for the LSTM networks. Too many hidden neurons may lead to high computation cost and over-fitting, while too few hidden neurons may cause undercutting. Also, the suitable number of hidden neurons is usually determined by the number of input samples. That is, the exemplary inventive gas monitoring system and method may need more hidden neurons for a model trained with a larger transient window. In this set of experiments, the exemplary inventive gas monitoring system and method fix the transient window size to be 0.2 s and vary the number of hidden neurons from 200 to 75. As shown in FIG. 13, having 100 hidden neurons gives the lowest average error rate, 0.08%. Also, in some embodiment, having 75 hidden neurons is sufficient for training a good model with an average error rate of 0.12% and having more hidden neurons doesn't significantly lower the error rate. On the other hand, in some embodiment, cutting down the number of hidden neurons even further, such as 50 or 25, leads to unstable training and much higher error rates. As such, in the rest of the description, the number of hidden neurons is fixed to 75.

Figure 14:
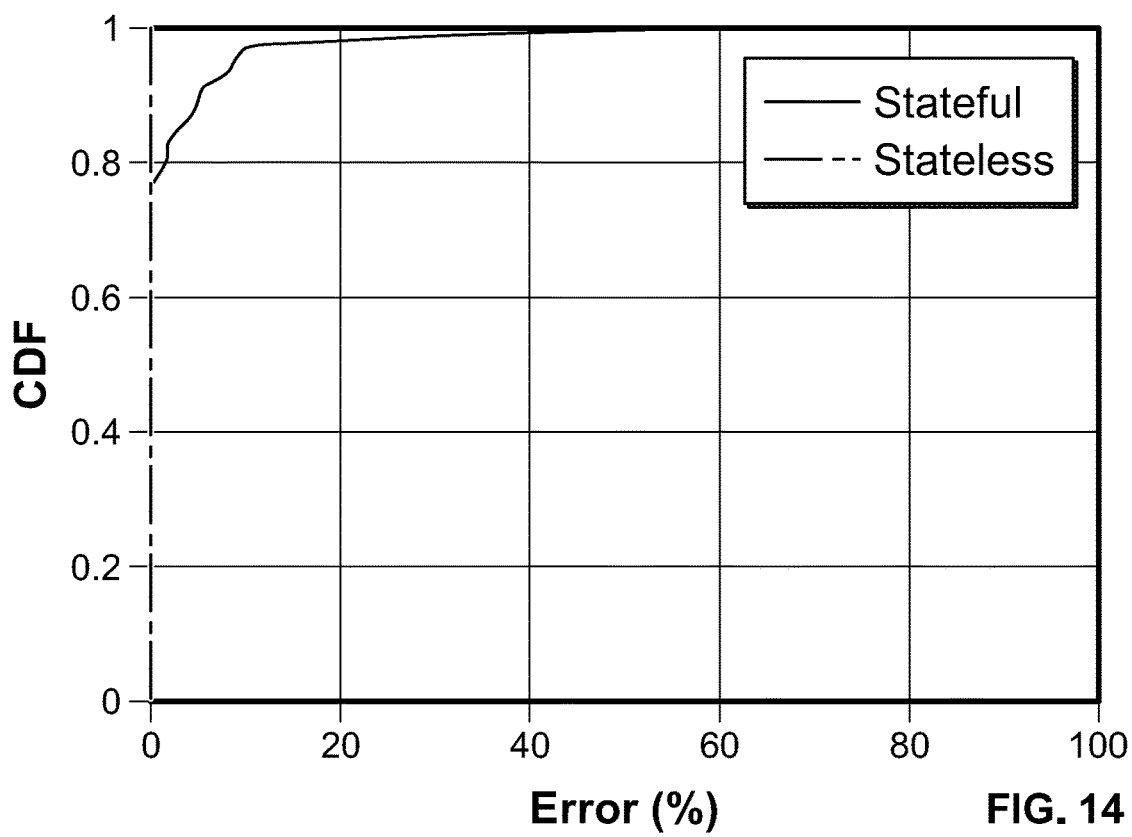
FIG. 14 shows a graph comparing stateful LSTM models and stateless LSTM models, with the stateless LSTM networks yielding lower error rates than the stateful LSTM networks.

Stateful vs stateless: Next, stateful networks versus stateless networks is compared. When processing a new batch of data, stateful networks maintain the states from the previous batch, while stateless networks reset to the initial states. FIG. 14 shows the cumulative distribution function (CDF) curves for both stateful and stateless versions of our model. In some embodiments, stateless LSTM networks perform better than the stateful counterparts. The average error rates are 0.12% and 2.95%, respectively. The reason is that the time dependencies are already well embedded inside of the transient responses, thus the exemplary inventive gas monitoring system and method can simply use stateless LSTM networks.

Comparing the LSTM Neural Networks with an Exponential Decay Model and a Linear Regression Model. Other regression methods, such as a simple linear regression model could also be a potential solution.

Figures 15A, 15B, 15C:
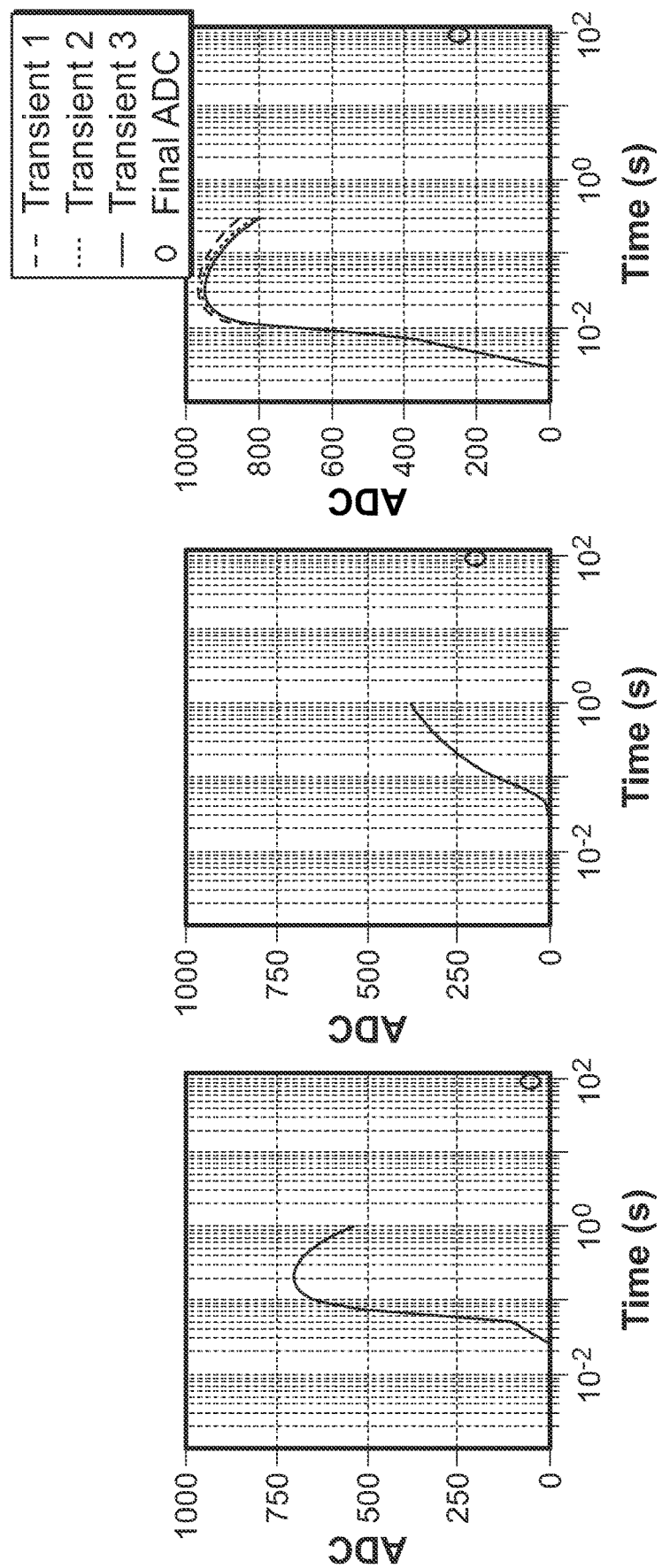
FIGS. 15(a) through 15(c) show graphs of time (s) versus ADC, wherein, within the 1-second window.

Two typical types of transient responses are illustrated in FIGS. 15 (a) and 15(b) according to some embodiments. FIG. 15(a) shows the transient response of a much-used sensor, whose pattern matches the observation in FIG. 7(b). Here, the ADC samples first increase, and then decrease. FIG. 15(b) shows the transient response of a sensor 12 which has not been used for a while, whose sensing layer 18 is mostly metal oxide. As a result, the reduction reaction is more drastic and takes a longer time to reach the equilibrium. In this case, it is observed that a monotonically increasing trend rather than an increase followed by a decrease as in (a). In addition, FIG. 15(c) shows a sensor's transient responses in different measurements under the same ammonia concentration the transient response varies from measurement to measurement.

An exponential decay model will fail in cases like (b), and thus the model is only applied to cases like in (a) and (c) in the comparison. Specifically, the exemplary inventive gas monitoring system and method adopt the following model:

$$y(t)=ae^{-bx(t)}+c, \quad (5)$$

where $x(t)$ is the input, $y(t)$ is the output, $a$, $b$ and $c$ are constant parameters. The exemplary inventive gas monitoring system and method may use the samples collected between 0.175 s and 1 s to estimate the parameters in the model. Once the parameters are obtained, the exemplary inventive gas monitoring system and method may estimate the equilibrium ADC sample at 100 s. It is found that the exponential decay model leads to very poor results for the considered transient window size. A linear regression model faces similar difficulties and yields large errors.

Table 3 shows a comparison of the exemplary inventive LSTM model against the exponential decay model and the linear regression model. The model as applied by the exemplary inventive gas monitoring system and method only requires data within a 0.2 s window size and the maximum error is as low as 0.45%. Both the exponential decay model and the linear regression model could not provide any reasonable results using a 1-second window size.

Table 3 compares the inventive exemplary approach against the exponential decay model and a linear regression model. Note that for the sake of fairness, the exemplary inventive gas monitoring system and method may evaluate our model using all the data available, but evaluate the other two models only using those data where such models can be applied such as the ones shown in FIG. 15(a) and FIG. 15(c). The results show that the model as applied in the exemplary inventive gas monitoring system and method can handle all three cases shown in FIG. 15 and performs much better than the other two models even the maximum error of this approach is smaller than the minimum error of the other two models.

TABLE 3

|  | Time (s) | Min (%) | Max (%) | Mean (%) |
|---|---|---|---|---|
| Exemplary approach | 0.2 | 0.00 | 0.45 | 0.12 |
| Exponential decay | 1 | >1*10$^5$ | >1*10$^5$ | >1*10$^5$ |
| Linear regression | 1 | >2*10$^3$ | >7*10$^4$ | >9*10$^4$ |

Testing the LSTM Networks with Different Test Data

It is demonstrated that the LSTM model as applied in the exemplary inventive gas monitoring system and method can work well on different test data. From all the 38 sensors, the exemplary inventive gas monitoring system and method randomly pick a single sensor and train a model with the data from this sensor. Then, the exemplary inventive gas monitoring system and method may evaluate the model using test data from the same sensor and test data from the other 37 sensors.

Figure 16:
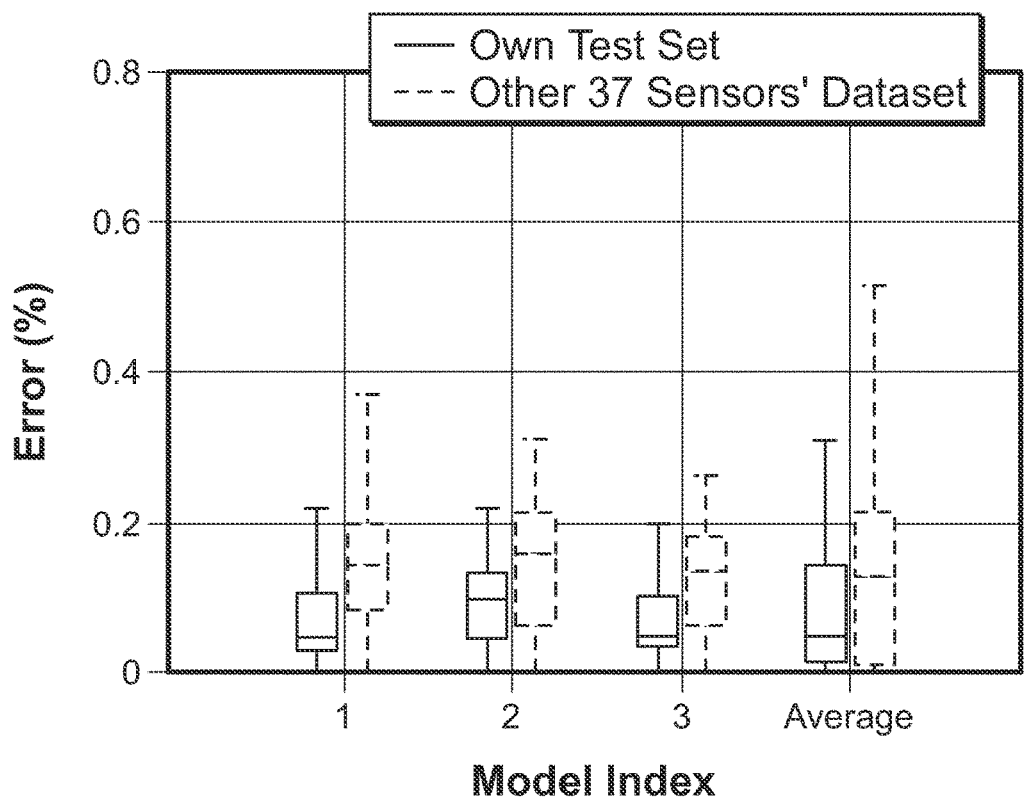
FIG. 16 shows a graph of model index versus error percentage (%), which show an evaluation of LSTM network performance using test data from different sensors, the results showing the model performs similarly when testing with same-sensor data or testing with different-sensor data.

The exemplary inventive gas monitoring system and method repeat this process for all the sensors and show the results in FIG. 16, which reports the performance of three models, each trained by a different sensor, as well as the performance averaged over all cases. The blue box plot represents the average error rate of the model using the test set from the same sensor and each orange box plot represents the results of the model using different test data. In general, it is observed that a very small performance difference between testing the LSTM networks as applied in the exemplary inventive gas monitoring system and method with same-sensor test data and testing with different-sensor test data the average error rate in the former case is 0.12% while the average error rate in the latter case is 0.20%. Although the variations in the sensors are large, there are consistent underlying hidden state representations among all our ammonia sensors that can be captured by LSTM neural networks.

Evaluation of the Power Law Model Based Calibration

In some embodiments, the exemplary inventive gas monitoring system and method may repeat the sensor calibration process i.e., mapping the equilibrium ADC to the corresponding ammonia level (as described in Section "Step III: Ammonia Concentration Calibration") using industrial calibrated ammonia gas at different concentrations and report the calibration results.

Figure 17:
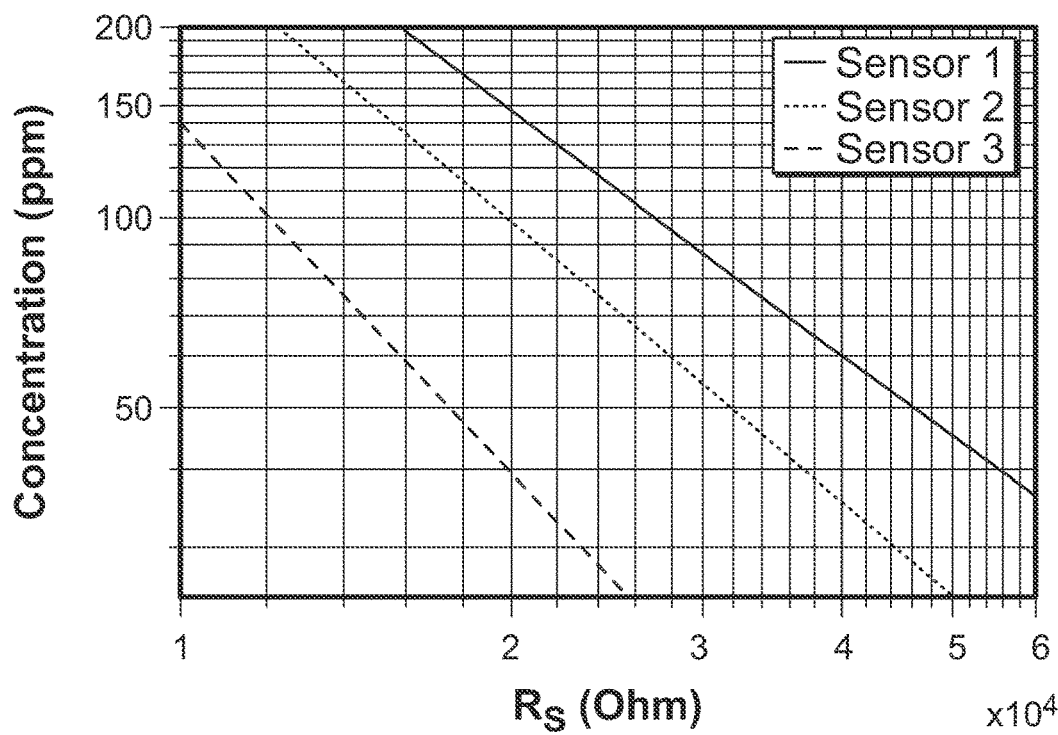
FIG. 17 is a graph showing an embodiment of calibration results for three sensors.

FIG. 17 shows example calibration results for 3 sensors. In some embodiments, the exemplary inventive gas monitoring system and method convert the ADC samples to the sensor's resistance according to Equation 4 and show the results in the log scale on both x and y axes. The mean absolute error across all 38 sensors is 9.38 ppm. Also, the sensor has different sensitivity to ammonia.

Exemplary Trials

A 4-month NIH Trial: In some embodiments, the exemplary inventive gas monitoring system and method is applied in a laboratory animal facility at National Institute of Neurological Disorders and Stroke (NINDS) and completed a 4-month trial. This trial involves 20 ventilated cages, and the exemplary inventive gas monitoring system and method deployed one ammonia sensor in each cage. The entire trial is divided into 6 cycles, with 21 days per cycle. All cages host 5 female mice that were 12 weeks old at the beginning of the trial. The mice are provided with bedding, standard food and reverse osmosis water. The exemplary inventive gas monitoring system and method measure the resultant ammonia concentration level continuously, once in every 3 hours.

Figure 18C:
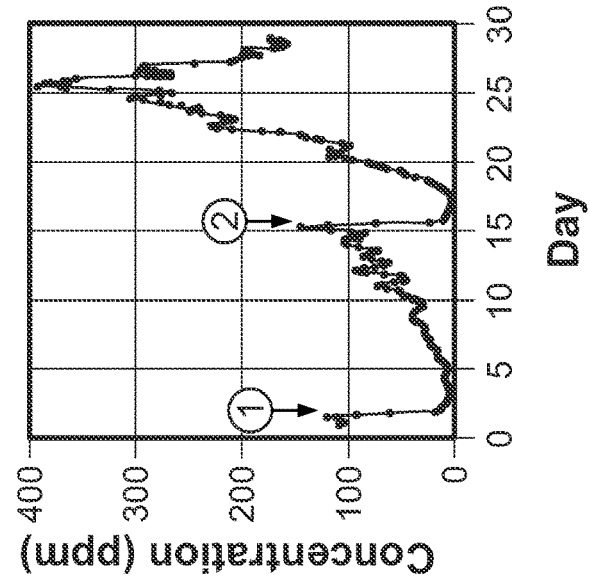
FIG. 18(c) shows a graph of days versus concentration (ppm), with an ammonia concentration trace of cage 6 in a 28 day period in a Cornell trail, with the circles showing the scheduled cage change events.
Figure 18B:
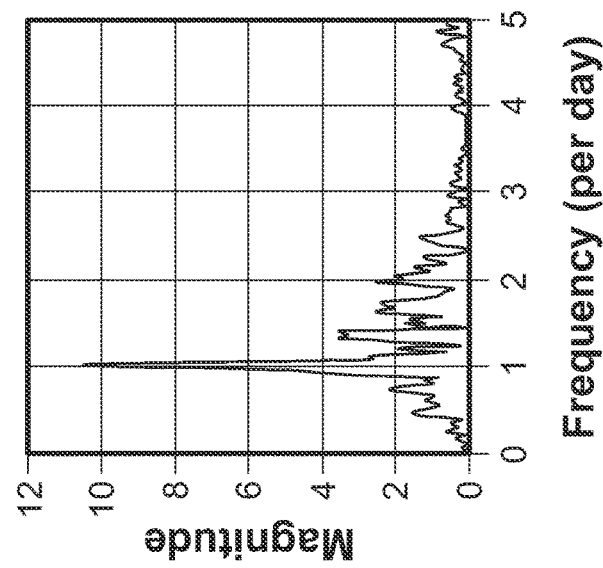
FIG. 18(b) shows a graph of frequency (days) versus magnitude, with removal of an obvious trend in FIG. 18(a) using a moving average and computing FFT results of the residual.
Figure 18A:
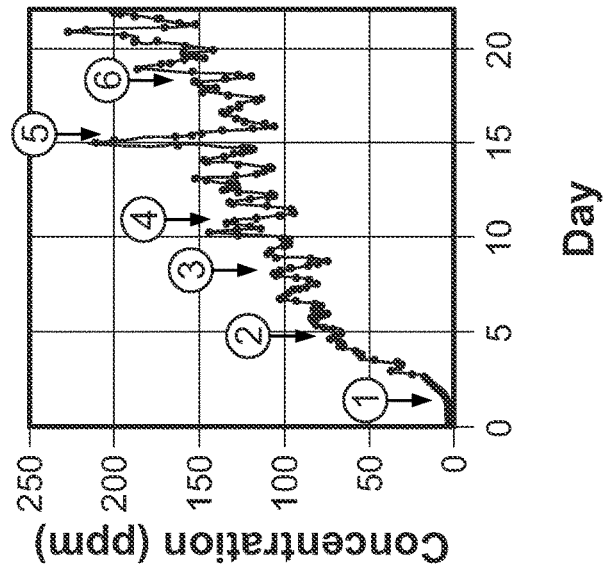
FIG. 18(a) shows a graph of days versus concentration (ppm) for an ammonia concentration trace in a 21-day cycle of cage 21 in an NIH trial, with circles marking the scheduled operations of changing the cage bedding.

FIG. 18(a) illustrates the results of the sensor measurements in a 21-day cycle for cage 11. During this cycle, the cage is not changed but the bedding is changed (also varied the bedding type) every Tuesday and Friday. All of the six change events are marked and numbered in FIG. 18(a). Also, on the same days when the bedding was changed, the exemplary inventive gas monitoring system and method measured adenosine triphosphate (ATP) released in duct cells, the amount of water consumed, etc. Since the cage remained the same during the entire cycle, the overall ammonia level continuously went up, except that after each bedding change the measured ammonia level decreased to a certain degree.

Even though the overall trend of the ammonia level is going up, it is observed a ne-grained periodic ammonia level fluctuation in FIG. 18(a). Further, the interval between two adjacent local peaks is 24 hours. This daily fluctuation may be caused by daily events in the environment, such as the building ventilation system. To confirm this observation, the exemplary inventive gas monitoring system and method remove the trend in the ammonia measurement trace and compute the FFT of the residual signal. Shown in FIG. 18(b), the residual signal has an obvious spike at once per day. Similarly, it is also observed the same phenomenon in the lab and in other trials that are conducted. Finally, it is noted that the above trend that is observed for cage 11 is common across all the cages.

A 3-month Cornell Trial: The second trial is at Cornell University and lasts for 3 months. The objective of the trial is to study the animals' breeding related behaviors. This trial involves 18 standard cages and we deployed one ammonia sensor in each cage. In this trial, the exemplary inventive gas monitoring system and method measure each cage's ammonia level continuously, once every 3 hours.

FIG. 18(c) illustrates the results for cage 6's measurements in a 28-day period. On day 1, the female mouse of the couple in the cage gave birth to 8 pups. On day 2, a first scheduled cage change moved the two adult mice to a new cage 6, while the pubs were transferred to another cage. Between day 2 and day 15, it is observed that the ammonia concentration in cage 6 increased. On day 16, a second scheduled cage change put the 8 pups back together with the parents in a new cage 6. After the second cage change, it is observed that a much faster increase of ammonia concentration in the cage as the number of mice was increased from 2 to 10. Further, the ammonia level increase from day 21 to day 25 became even faster. This is because in general day 21 is considered a pub's weaned age after that, they can eat and latrine on their own. Thus, the production of waste in cage 6 increased and the ammonia production increased as well. After day 25, the ammonia level decreased due to some undocumented cage change events.

Discussion about the ammonia measurement frequency in real-world applications: Lab animals are used for a variety of research purposes. The ammonia concentration depends on several factors the type of the cages (static, air ventilated), the type of the bedding, the number of mice/rats, the type of experiments (e.g., drug tests may disturb digest behavior), etc. Thus, it is hard to have an exact measurement frequency that satisfies all the cases. For example, a diabetic model mouse might require sampling on the order of a few hours, while a single mouse in a cage might be 1 to 2 days. The exemplary inventive gas monitoring system and method can satisfy the need of frequent ammonia monitoring and still can last for at least 20 years assuming one measurement in every three hours.

It is noted that none of the existing systems are accurate, low-power, low-cost, compact and automatic all at the same time. For example, ammonia test strips are inaccurate; ammonia test tubes are expensive; metal oxide sensors are power-consuming and bulky; electrical-chemical sensors and fiber-coupled optical sensors are power-consuming, expensive and bulky. Also, all the existing ammonia monitoring methods require extensive manual operations for large-scale lab cage monitoring.

Ammonia test strips: An ammonia test strip typically has two layers. When a moist ammonia test strip is dipped into a cage, the first layer quickly picks up ammonia in the air onto its moist side. Next, the alkaline chemical, on the other side of the first layer, release ammonia in the gaseous state to the second layer. The second layer has a chemical reagent which reacts with ammonia gas. This reaction leads to a pH change and shows in the form of color change. Finally, the color of the ammonia strip is compared against a standard color chart and estimate the ammonia concentration empirically. The major advantage of ammonia test strips is low-cost. However, the measurement is neither accurate nor convenient. In practice, at high concentration (>50 ppm), the color of an ammonia strip may change quickly in one or two seconds because ammonia is a highly volatile gas. Also, the standard color chart only shows colors at a few concentrations usually 0, 10, 25, 50, 100 ppm. Thus, it's rather difficult to get an accurate measurement using ammonia test strips.

Ammonia test tubes: An ammonia test tube is typically combined with a hand-held device. This device typically has an air pump, a meter which reads the color change, and a large battery. Starting from each experiment, the pump draws a fixed amount of air and mix the air with the chemical reagent in the tube. Instead of mapping the color, the device measures the duration of the color change and maps the duration to a concentration. Ammonia test tubes provide a measurement of 10% accurate. However, the device requires manual operation and the cost per measurement is expensive (about $10).

Metal oxide sensors: At an elevated temperature, usually in a range of about 100° C. to about 400° C., metal oxide may have reduction reaction with ammonia and be converted to metal. Meanwhile, metal may have oxidization reaction with oxygen and be converted back to metal oxide. Over time, the reduction and the oxidization reaction reach a chemical equilibrium. Then, the exemplary inventive gas monitoring system and method can measure the sensor resistance and map it to ammonia concentration. The sensor is reusable and accurate. However, the sensor requires minutes heating thus is power consuming. Also, like others, the existing metal oxide sensors are built into handheld devices and requires manual operation.

Electrical-chemical (EC) sensors: A EC sensor consists of three electrodes: a reacting electrode, a counter electrode and a reference electrode. Similar as metal oxide sensors, the reacting electrode in a EC sensor have reduction-oxidation reaction with ammonia at high temperature. The reaction generates electric current between the reacting electrode and the counter electrode. The exemplary inventive gas monitoring system and method can map the voltage across the electrodes with respect to the reference electrode to an ammonia concentration. EC sensors are accurate, but expensive, power consuming and have limited lifetime.

Fiber-coupled optical sensors: This type of sensor consists of a glass chamber which contains a multimode waveguide with carefully coated chemical dye. Outside the chamber, two light sources of particular wavelength shoot lights towards the sensor. As ammonia appears in the glass chamber, the dye changes its color due to the reversible chemical reaction. Such color change greatly changes the attenuation of the light at one wavelength, but not the attenuation of the light at the other wavelength. Then, an algorithm can map the relative attenuation ratio between two light wavelengths to an ammonia concentration. This sensor is reusable. However, the sensor requires expensive calibration and can be easily affected by other common gases like carbon dioxide. The entire system is expensive and bulky. Also, both sensor systems require extensive manual operations as well. As such, they are not suitable for large-scale lab cage monitoring.

In an embodiment, a low-power, automatic, accurate and wireless ammonia monitoring system that uses metal oxide sensors is developed and evaluated. The exemplary inventive gas monitoring system and method provided by the present invention greatly shortens the heating period and use the transient measurements in the short heating window to predict the final value at the equilibrium state. The prediction model as applied in the exemplary inventive gas monitoring system and method is centered around LSTM neural networks. This approach can cut down the overall energy assumption by about 99.6%. Through extensive experiments, it is shown that the prediction model is accurate across 38 prototype sensors the average prediction error rate of is 0.12% and the average absolution error against the calibrated gas is 9.38 ppm. Also, the prediction model can be used to accurately predict for new sensors even though the data from these sensors were not part of the training data.

Although the various embodiments of the present invention detailed herein describes or illustrates particular operations as occurring in a particular order, the present invention contemplates any suitable operations occurring in any suitable order. Moreover, the present invention contemplates any suitable operations being repeated one or more times in any suitable order. Although the present invention describes or illustrates particular operations as occurring in sequence, the present invention contemplates any suitable operations occurring at substantially the same time, where appropriate. Any suitable operation or sequence of operations described or illustrated herein may be interrupted, suspended, or otherwise controlled by another process, such as an operating system or kernel, where appropriate. The acts can operate in an operating system environment or as stand-alone routines occupying all or a substantial part of the system processing.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same.

What is claimed is:

1. A method, comprising:
    heating a metal oxide sensor for a predetermined period of time for the metal oxide sensor to interact with a surrounding gas, wherein the metal oxide sensor includes a heater;
    sampling, during the heating, transient resistance values of the metal oxide sensor to obtain sampled transient resistance values;
    determining an electrical resistance of the metal oxide sensor in a chemical equilibrium state of the interaction of the metal oxide sensor and the surrounding gas, wherein determining the equilibrium electrical resistance is based at least upon the sampled transient resistance values and via applying a neural network; and
    determining a concentration level of the surrounding gas at the chemical equilibrium state by mapping the determined electrical resistance to a corresponding concentration level of the surrounding gas.

2. The method of claim 1, wherein the metal oxide sensor is heated to a temperature between 100 to 400° C.

3. The method of claim 1, wherein the predetermined period of time is between 1-100 milliseconds.

4. The method of claim 1, wherein the chemical equilibrium is when a metal oxide on a sensing layer of the metal oxide sensor reduction-oxidation ("redox") reacts with the surrounding gas and oxygen simultaneously and the redox process reaches its chemical equilibrium.

5. The method of claim 1, wherein the transient resistance values of the metal oxide sensor are analog-to-digital converter (ADC) values and the predicted electrical resistance is a final ADC value of the metal oxide sensor.

6. The method of claim 1, wherein the step of sampling the transient resistance values includes:
    activating the metal oxide sensor;
    activating, by the metal oxide sensor, the heater inside of the metal oxide sensor;
    measuring the transient resistance values at a predetermined power during a first period of time;
    collecting the transient resistance values that are transient responses;
    deactivating, by the metal oxide sensor, the heater; and
    deactivating the metal oxide sensor for a second period of time till a next duty cycle.

7. The method of claim 1, wherein the first period of time is a first second of heating the metal oxide sensor.

8. The method of claim 1, wherein the second period of time is with a range from 10 minutes to 1 day.

9. The method of claim 1, wherein the sampled transient values are transmitted wirelessly before being preprocessed.

10. The method of claim 1, further comprising:
    preprocessing the sampled transient resistance values, wherein the preprocessing comprises
        eliminating the sampled transient values from measurements that do not have a first 5 transient resistance samples or the final sample; and
        recovering missing data from transmission of the sampled transient resistance values by applying a spline interpolation technique.

11. The method of claim 1, wherein the neural network is a long short term memory (LSTM) neural network.

12. The method of claim 11, wherein the LSTM neural network includes an LSTM layer and a fully connected layer.

13. The method of claim 12, wherein the LSTM layer at time n processes an input data $x_n$ together with cell state $c_{n-1}$ and previous output $h_{n-1}$, and sends output $h_n$ to the fully connected layer, and the fully connected layer generates a final output for the LSTM neural network.

14. The method of claim 1, wherein determining the electrical resistance of the metal oxide sensor in the chemical equilibrium state via applying the LSTM neural network comprises
    preparing the sampled transient resistance values to make them suitable for the LSTM neural network.

15. The method of claim 14, wherein preparing the sampled transient resistance values comprises:

computing first derivatives of the sampled transient resistance values configured to cause the LSTM neural network to learn desired patterns from the sampled transient resistance values; and scaling the computed derivative to a numerical range.

16. The method of claim 1, wherein the surrounding gas is selected from a group of gases consisting of: ammonia, ethanol, hydrogen sulphide, methane, propane, iso-butane, nitrogen dioxide, and carbon monoxide.

17. The method of claim 1, wherein mapping the determined electrical resistance at the chemical equilibrium to the corresponding gas concentration level comprises:

placing multiple sensors into a container with fresh air, wherein the container has one gas connector on each side and has high corrosive resistance to the surrounding gas;

connecting one of the gas connectors to a valve controlled cylinder that contains calibrated gas while leaving the other one of the gas connectors to the open air;

continuously releasing the calibrated gas until the calibrated gas in the container reaches a same gas concentration as that inside of the valve controlled cylinder;

repeating the placing, connecting, continuously releasing steps with different gas concentration levels; and fitting the different gas concentration levels into a curve-fitting model.

18. A system, comprising:

a metal oxide sensor comprising a heater, an embedded heating layer, and a sensing layer, wherein the sensing layer is configured to interact with a surrounding gas and the heater is configured to heat the embedded heating layer for a predetermined period of time for the metal oxide sensor to interact with the surrounding gas;

a processor;

a non-transitory computer readable storage medium storing thereon program logic for execution by the processor, wherein, when executing the program logic, the processor is configured to:

heat a metal oxide sensor for a predetermined period of time for the metal oxide sensor to interact with a surrounding gas, wherein the metal oxide sensor comprising a heater;

sample, during the heating, transient resistance values of the metal oxide sensor to obtain sampled transient resistance values;

determine an electrical resistance of the metal oxide sensor in a chemical equilibrium state of the interaction of the metal oxide sensor and the surrounding gas to calculate a determined electrical resistance, wherein determining is based at least upon the sampled transient resistance values and via applying a neural network; and determine a concentration level of the surrounding gas at the chemical equilibrium state by mapping the determined electrical resistance to a corresponding concentration level of the surrounding gas.

19. The system of claim 18, wherein the metal oxide sensor further comprises a machined diaphragm base layer.

20. The system of claim 18, wherein the processor is configured to sample the transient resistance values comprises:

activate the metal oxide sensor;

activate, by the metal oxide sensor, the heater inside of the metal oxide sensor;

measure the transient resistance values at a predetermined power during a first period of time;

collect the transient resistance values that are transient responses;

deactivate, by the metal oxide sensor, the heater; and deactivate the metal oxide sensor for a second period of time till a next duty cycle.

21. The system of claim 18, wherein the processor is configured to determine the concentration level of the surrounding gas at the chemical equilibrium state by mapping the determined electrical resistance to a corresponding concentration level of the surrounding gas comprises:

place multiple sensors into a container with fresh air, wherein the container has one gas connector on each side and has high corrosive resistance to the surrounding gas;

connect one of the gas connectors to a valve controlled cylinder that contains calibrated gas while leaving the other one of the gas connectors to the open air;

continuously release the calibrated gas until the calibrated gas in the container reaches a same gas concentration as that inside of the valve controlled cylinder;

repeating the place, connect, continuously release steps with different gas concentration levels; and fit the different gas concentration levels into a curve-fitting model.

22. The system of claim 18, wherein the neural network is a long short term memory (LSTM) neural network.

23. The system of claim 22, wherein the LSTM neural network includes an LSTM layer and a fully connected layer.

* * * * *